(12) United States Patent
Marton et al.

(10) Patent No.: US 11,452,671 B2
(45) Date of Patent: *Sep. 27, 2022

(54) VIBRATION AND HEAT GENERATION APPARATUS FOR USE WITH COMPRESSION WRAPS

(71) Applicant: Hyper Ice, Inc., Irvine, CA (US)

(72) Inventors: Robert Marton, Yorba Linda, CA (US); Anthony Katz, Laguna Niguel, CA (US)

(73) Assignee: Hyper Ice, Inc., Irvine, CA (US)

( * ) Notice: Subject to any disclaimer, the term of this patent is extended or adjusted under 35 U.S.C. 154(b) by 397 days.

This patent is subject to a terminal disclaimer.

(21) Appl. No.: 16/741,317

(22) Filed: Jan. 13, 2020

(65) Prior Publication Data

US 2020/0170880 A1    Jun. 4, 2020

Related U.S. Application Data

(63) Continuation of application No. PCT/US2018/039772, filed on Jun. 27, 2018, which
(Continued)

(51) Int. Cl.
*A61H 23/02* (2006.01)
*A61H 1/00* (2006.01)
*A61F 7/00* (2006.01)

(52) U.S. Cl.
CPC ............. *A61H 23/02* (2013.01); *A61F 7/007* (2013.01); *A61H 1/00* (2013.01); *A61H 1/008* (2013.01);
(Continued)

(58) Field of Classification Search
CPC .......... A61H 1/00; A61H 1/006; A61H 1/008; A61H 7/001; A61H 23/00; A61H 23/006;
(Continued)

(56) References Cited

U.S. PATENT DOCUMENTS 4,396,011 A    8/1983   Mack et al.
5,107,832 A    4/1992   Guibert et al.
(Continued)

FOREIGN PATENT DOCUMENTS

CN    103356258 A    10/2013
CN    203564652 U     4/2014
(Continued)

OTHER PUBLICATIONS http://www.alibaba.com/product-detail/Far-infrared-Arthrosis-hot-message.apparatus_6005767663827.html—accessed online Jun. 8, 2015.
(Continued)

*Primary Examiner* — Tu A Vo
*Assistant Examiner* — Benjamin M. Kusiak
(74) *Attorney, Agent, or Firm* — Patterson Intellectual Property Law, P.C.; Jerry Turner Sewell

(57) ABSTRACT

A system applies compression, vibration and heat to a body part of a person. The system includes a portable vibration and heat generation apparatus having a flexible support platform and a bag-like enclosure extending from the support platform. A cylindrical control unit is mounted to the support platform and extends perpendicularly from the support platform. The control unit has a diameter of between 50 millimeters and 100 millimeters. The control unit houses electronic circuitry and at least one battery. Four vibration pods extend from the support platform into the bag-like structure. The bag-like structure also houses a heat generation unit. The control unit extends through a circular bore in a compression wrap. The compression wrap is securable to a body part with a distal wall of the bag-like enclosure against the body part. The system selectively applies vibration, heat or a combination of vibration and heat to the body part.

9 Claims, 24 Drawing Sheets

Related U.S. Application Data is a continuation of application No. 15/650,410, filed on Jul. 14, 2017, now Pat. No. 10,524,978.

(52) U.S. Cl.
CPC . *A61H 23/0254* (2013.01); *A61H 2201/0157* (2013.01); *A61H 2201/0207* (2013.01); *A61H 2201/10* (2013.01); *A61H 2201/165* (2013.01); *A61H 2201/169* (2013.01); *A61H 2201/5046* (2013.01); *A61H 2201/5082* (2013.01); *A61H 2201/5097* (2013.01); *A61H 2205/062* (2013.01); *A61H 2205/088* (2013.01); *A61H 2205/102* (2013.01)

(58) Field of Classification Search
CPC ............. A61H 23/02; A61H 23/0254; A61H 23/0263; A61H 23/0272; A61H 2201/0153; A61H 2201/0157; A61H 2201/0173; A61H 2201/0176; A61H 2201/0188; A61H 2201/02; A61H 2201/0207; A61H 2201/0221; A61H 2201/022; A61H 2201/0228; A61H 2201/0235; A61H 2201/10; A61H 2201/12; A61H 2201/1207; A61H 2201/1215; A61H 2201/1616; A61H 2201/1621; A61H 2201/1626; A61H 2201/163; A61H 2201/1638; A61H 2201/1642; A61H 2201/1645; A61H 2201/165; A61H 2201/1652; A61H 2201/1654; A61H 2201/5002; A61H 2201/5007; A61H 2201/501; A61H 2201/5023; A61H 2201/5035; A61H 2201/5043; A61H 2201/5046; A61H 2201/5082; A61H 2201/5094; A61H 2201/169; A61H 2205/06; A61H 2205/10; A61H 2205/12; A61H 2205/062; A61H 2205/088; A61H 2205/102
USPC ........ 601/46, 49, 56, 60, 64, 65, 67, 69, 70, 601/71, 107, 15, 18; 607/96, 108–112
See application file for complete search history.

(56) References Cited

U.S. PATENT DOCUMENTS

| | | | |
|---|---|---|---|
| 5,584,797 A | 12/1996 | Yoo | |
| 8,523,793 B1 * | 9/2013 | Waldon, Sr. ........... | A61H 23/02 601/87 |
| 9,192,326 B2 | 11/2015 | Kahn et al. | |
| 9,289,323 B2 | 3/2016 | Marton et al. | |
| D811,613 S | 2/2018 | Marton et al. | |
| D811,614 S | 2/2018 | Marton et al. | |
| 10,159,623 B2 | 12/2018 | Leftly | |
| 2001/0007952 A1 | 7/2001 | Shimizu | |
| 2002/0046232 A1 | 4/2002 | Adams et al. | |
| 2002/0111570 A1 | 8/2002 | Cutler et al. | |
| 2004/0133133 A1 | 7/2004 | Dreimann et al. | |
| 2007/0255187 A1 | 11/2007 | Branch | |
| 2009/0143707 A1 | 6/2009 | Strahl | |
| 2012/0022411 A1 | 1/2012 | Wu | |
| 2012/0046579 A1 | 2/2012 | Radl et al. | |
| 2012/0253236 A1 * | 10/2012 | Snow ................... | A61N 5/0618 601/2 |
| 2013/0041297 A1 | 2/2013 | Garcia et al. | |
| 2013/0261659 A1 | 10/2013 | Lorenzo | |
| 2014/0046232 A1 | 2/2014 | Sham et al. | |
| 2014/0309563 A1 * | 10/2014 | Park ..................... | A61F 7/02 601/48 |
| 2014/0364778 A1 | 12/2014 | Leftly et al. | |
| 2015/0305974 A1 | 10/2015 | Ehrenreich et al. | |
| 2016/0235614 A1 * | 8/2016 | Kay ..................... | A61F 7/103 |
| 2017/0087005 A1 | 3/2017 | Na et al. | |
| 2019/0142689 A1 * | 5/2019 | Marty .................... | A61H 15/02 601/112 |

FOREIGN PATENT DOCUMENTS

| | | | | |
|---|---|---|---|---|
| CN | 204995778 U | 1/2016 | | |
| CN | 205125121 U | 4/2016 | | |
| JP | H02-141445 U | 11/1990 | | |
| JP | 203204982 A | 7/2003 | | |
| JP | 2003204982 A | 7/2003 | | |
| JP | 2005312761 A | 11/2005 | | |
| JP | 2011188921 A | 9/2011 | | |
| JP | 2013532575 A | 8/2013 | | |
| JP | 2016521999 A | 7/2016 | | |
| KR | 20020062521 A | 7/2002 | | |
| TW | 576197 | 2/2002 | | |
| TW | 576197 U | 2/2004 | | |
| WO | 2016051414 A1 | 4/2016 | | |
| WO | 2017069509 A1 | 4/2017 | | |
| WO | WO-2017069509 A1 * | 4/2017 | ............... | A61F 7/00 |

OTHER PUBLICATIONS

Machine Translation of WO 2017/069509 A1.
International Search Report and Written Opinion for International Application No. PCT/US2018/039772, dated Oct. 18, 2018, 11 pages.
Search Report for Taiwanese Application No. 107232086, dated Dec. 12, 2019.
Office Action for Taiwanese Application No. 107123086, dated Jan. 13, 2020.
Translation of Office Action for Taiwanese Application No. 107123086, dated Jan. 13, 2020.
Google Patents Translation of CN204995778U.
Google Patents Translation of CN205125121U.
Search Report for corresponding patent application No. TW 107123086, dated Jan. 13, 2020, 1 page.
Extended European Search Report of corresponding European Patent No. 18831605.3, dated Jul. 15, 2021, 10 pages.
Japanese Office Action for corresponding patent application No. 2020-501370, dated Oct. 6, 2020, 10 pages.
Office Action for corresponding CN 201880059789.4, dated Oct. 21, 2020, 14 pages.

* cited by examiner

VIBRATION AND HEAT GENERATION APPARATUS FOR USE WITH COMPRESSION WRAPS

RELATED APPLICATIONS

This application is a continuation of International Application No. PCT/US2018/039772 filed on Jun. 27, 2018, which claims priority from U.S. patent application Ser. No. 15/650,410 filed on Jul. 14, 2017 (now U.S. Pat. No. 10,524,978), which are incorporated herein in their entireties.

FIELD OF THE INVENTION

The present invention is in the field of therapeutic devices, and, more particularly, is in the field of devices that provide vibration and heat to selected portions of a body.

BACKGROUND OF THE INVENTION

The applications of vibration and heat to tired and injured tissues are known to be therapeutic to the tissues. Various devices have been used to provide vibration, to provide heat or to provide a combination of vibration and heat. Many of the devices require continual manual application of the device. Other devices are configured to provide vibration, heat, or both vibration and heat to specific locations of the body by attachment to the location. Such devices require a person to purchase a different version of the device for each body location requiring therapy.

SUMMARY OF THE INVENTION

A need exists for a therapeutic vibration and heat apparatus that can be attached to different locations on a body without requiring a different device configuration for each location.

One aspect of the embodiments disclosed herein is a system that applies compression, vibration and heat to a body part of a person. The system includes a portable vibration and heat generation apparatus having a flexible support platform and a bag-like enclosure extending from the support platform. A cylindrical control unit is mounted to the support platform and extends perpendicularly from the support platform. The control unit has a diameter of between 50 millimeters and 100 millimeters. The control unit houses electronic circuitry and at least one battery. Four vibration pods extend from the support platform into the bag-like structure. The bag-like structure also houses a heat generation unit. The control unit extends through a circular bore in a compression wrap. The compression wrap is securable to a body part with a distal wall of the bag-like enclosure against the body part. The system selectively applies vibration, heat or a combination of vibration and heat to the body part.

Another aspect of the embodiments disclosed herein is a portable vibration and heat generation apparatus. The apparatus comprises a flexible support platform, a cylindrical control unit, a plurality of vibration pods, a heat generation unit, and a bag-like enclosure. The cylindrical control unit is mounted to a central portion of the support platform and extends perpendicularly from the support platform in a first direction. The control unit has a diameter of between 50 millimeters and 100 millimeters. The control unit houses electronic circuitry and at least one battery. The plurality of vibration pods are attached to the flexible support platform. Each vibration pod extends from the support platform in a second direction, which second direction is opposite the first direction, the vibration pods are electrically connected to the control unit. The heat generation unit is positioned below the vibration pods. The heat generation unit electrically connected to the control unit. The bag-like enclosure is attached to the support platform and encloses the plurality of vibration pods and the heat generation unit. The bag-like enclosure has a distal wall. The heat generation unit is positioned adjacent to the distal wall. In certain embodiments, each vibration pod includes an electrical motor having a shaft coupled to an eccentric mass. In certain embodiments, four vibration pods are arranged generally symmetrically about the cylindrical control unit. In certain embodiments, the heat generation unit comprises at least one resistance heating wire secured to a flexible sheet. The resistance heating wire generates heat when a current flows through the heating wire. In certain embodiments, the heat generation unit is operable at at least a first temperature setting, a second temperature setting and a third temperature setting. In certain embodiments, the control unit is responsive to a signal received via a wireless communication interface. For example, in certain embodiments, the wireless communication interface is a Bluetooth interface. In certain embodiments, the flexible support platform, the control unit and the bag-like enclosure have sizes and shapes selected to cause the vibration and heat generation apparatus to resemble a therapeutic ice bag.

Another aspect of the embodiments disclosed herein is a system for applying compression, vibration and heat to a body part of a person. The system comprises a portable vibration and heat generation apparatus and a compression wrap. The portable vibration and heat generation apparatus comprises a flexible support platform, a cylindrical control unit, a plurality of vibration pods, a heat generation unit and a bag-like enclosure. The cylindrical control unit is mounted to a central portion of the support platform and extends perpendicularly from the support platform in a first direction. The control unit has a diameter of between 50 millimeters and 100 millimeters. The control unit houses electronic circuitry and at least one battery. The plurality of vibration pods are attached to the flexible support platform. Each vibration pod extends from the support platform in a second direction, which second direction is opposite the first direction. The vibration pods are electrically connected to the control unit. The heat generation unit is positioned distal to the vibration pods. The heat generation unit is electrically connected to the control unit. The bag-like enclosure is attached to and extends distally from the support platform. The bag-like enclosure encloses the plurality of vibration pods and the heat generation unit. The bag-like enclosure has a distal wall. The heat generation unit is positioned adjacent to the lower wall. The compression wrap comprises a unitary sheet of elastic material having a central body with straps extending therefrom. The central body includes at least one bore that receives the cylindrical control unit of the portable vibration and generation apparatus therethrough. The straps of the compression wrap are positionable with respect to the body part of the person to secure the distal wall of the bag-like enclosure of the portable vibration and generation apparatus against the body part to apply heat from the heat generation unit to the body part and to apply vibration from the vibration pods to the body part. In certain embodiments, the flexible support platform, the control unit and the bag-like enclosure have sizes and shapes selected to cause the portable vibration and heat generation apparatus to resemble a therapeutic ice bag.

Another aspect of the embodiments disclosed herein is a system for applying a combination of compression, vibration and heat to a body part of a person. The system comprises a portable vibration and heat generation apparatus and a compression wrap. The portable vibration and heat generation apparatus includes a flexible support platform, a bag-like enclosure, a cylindrical control unit, a plurality of vibration pods and a heat generation unit. The flexible support platform has an outer perimeter. The bag-like enclosure has a perimeter attached to the outer perimeter of the support platform. The bag-like enclosure extends distally from the support platform in a first direction to a distal wall. The cylindrical control unit is mounted to the support platform and extends perpendicularly proximally from the support platform in a second direction opposite the first direction. The control unit has a diameter of between 50 millimeters and 100 millimeters. The control unit houses electronic circuitry and at least one battery. The control unit includes a panel having a plurality of touch responsive areas thereon to receive commands to control the electronic circuitry. Each vibration pod has at least a portion extending from the support platform in the first direction and enclosed within the bag-like structure. The heat generation unit is enclosed within the bag-like structure and is positioned proximate to the distal wall of the bag-like structure. The compression wrap has a bore formed therethrough. The cylindrical control unit of the portable vibration and heat generation apparatus extends through the bore. The compression wrap is securable to a body part with the distal wall of the bag-like enclosure against the body part. In certain embodiments, the flexible support platform, the control unit and the bag-like enclosure have sizes and shapes selected to cause the portable vibration and heat generation apparatus to resemble a therapeutic ice bag.

BRIEF DESCRIPTIONS OF THE DRAWINGS

The foregoing aspects and other aspects of the disclosure are described in detail below in connection with the accompanying drawings in which:

FIG. 1 illustrates a top perspective view of a vibration and heat generation apparatus that can be applied to different locations of body, the apparatus including a vibration generation mechanism and a heat generation mechanism housed within a flexible enclosure, the apparatus further including a control unit housed within a generally cylindrical enclosure and extending from an upper flexible support structure;

Figure 27:
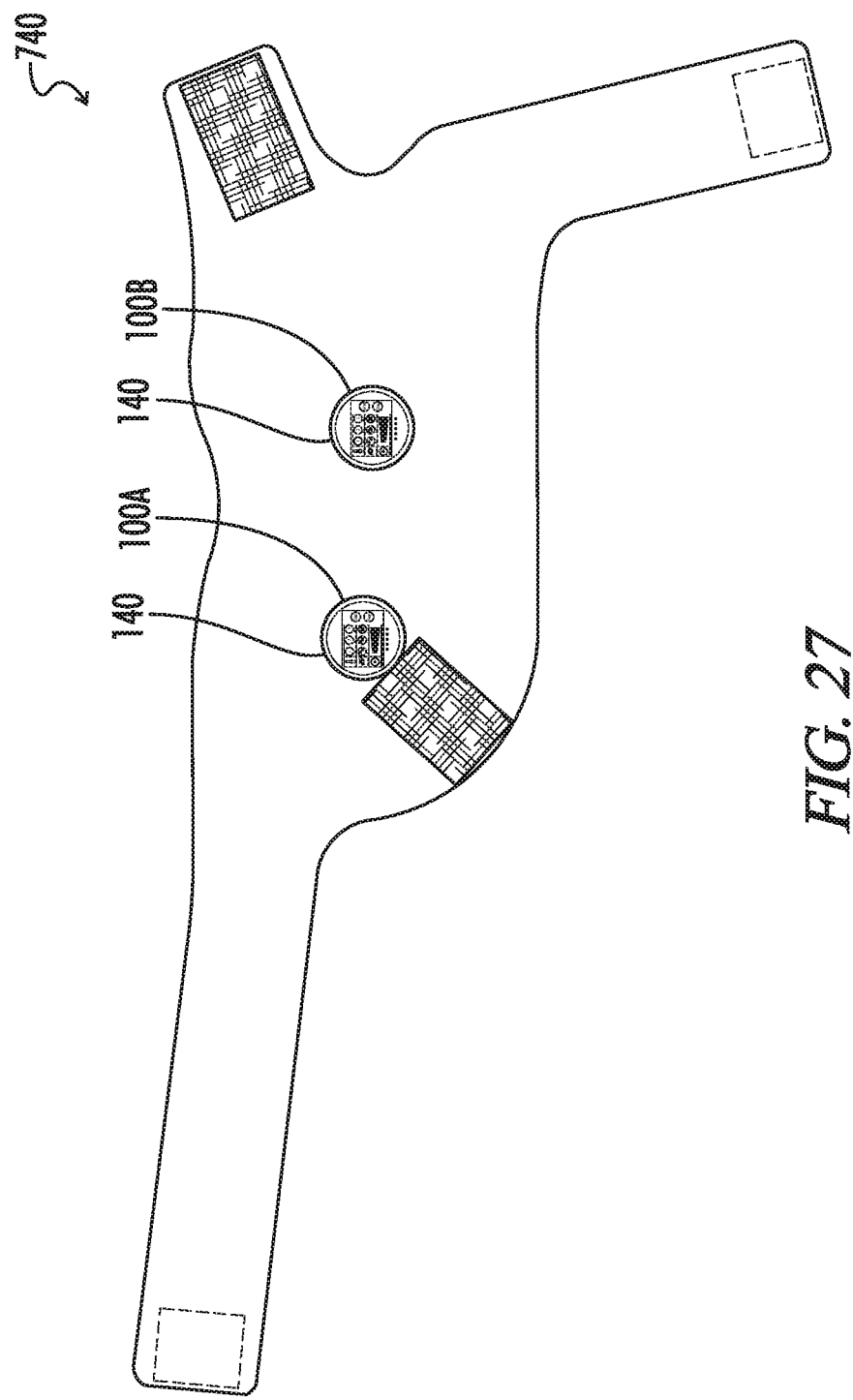
FIG. 27 illustrates an elevation view of the compression wrap of FIG. 24 with a control unit of a first vibration and heat generation unit of FIG. 1 extending through the first circular bore and with a control unit of a second vibration and heat generation unit of FIG. 1 extending through the second circular bore.
Figure 28:
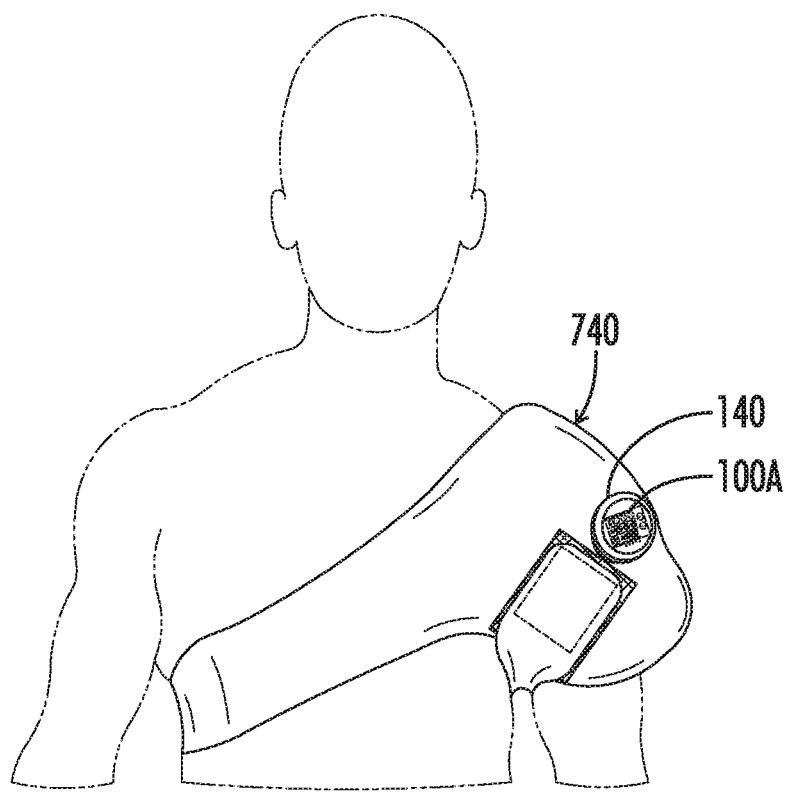
Figure 29:
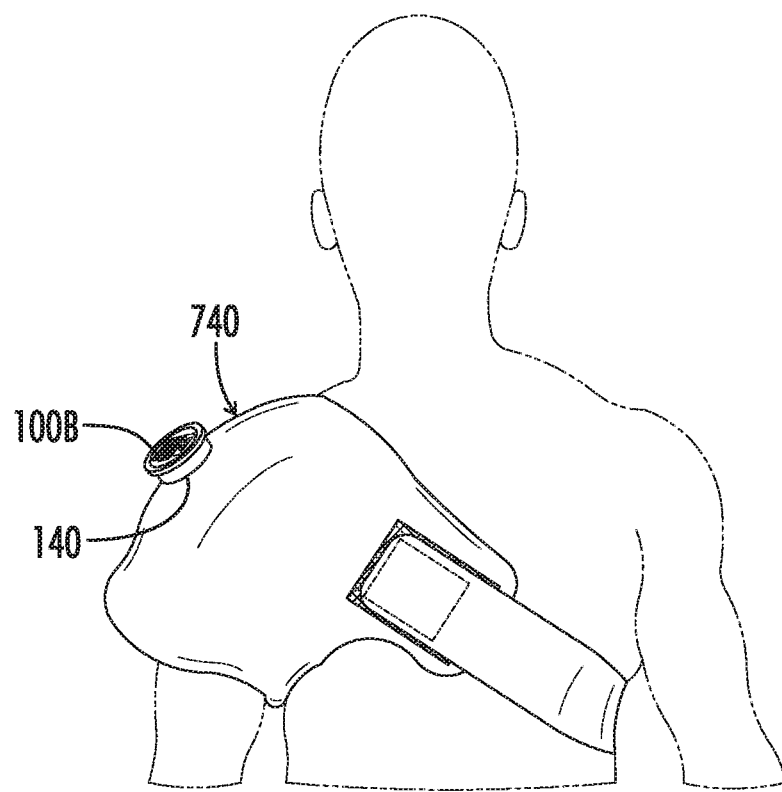

FIG. 28 illustrates a front perspective view of the compression wrap and the two vibration and heat generation units of FIG. 27 secured to the left shoulder of a person, the view showing the first vibration and heat generation unit positioned proximate to the front of the person's left shoulder; and FIG. 29 illustrates a front perspective view of the compression wrap and the two vibration and heat generation units of FIG. 27 secured to the left shoulder of a person, the view showing the second vibration and heat generation unit positioned proximate to the rear of the person's left shoulder.

DESCRIPTION OF ILLUSTRATED EMBODIMENTS

A vibration and heat generation apparatus 100 is illustrated in FIGS. 1-18. As described below, the vibration and heat generation apparatus can be applied to different locations of body. The apparatus can apply vibration to a selected location of the body, can apply heat to the selected location of the body, and can apply a combination of vibration and heat to the selected location of the body. The apparatus is particularly adapted to be used with compression wraps, which are also described below.

Figure 1:
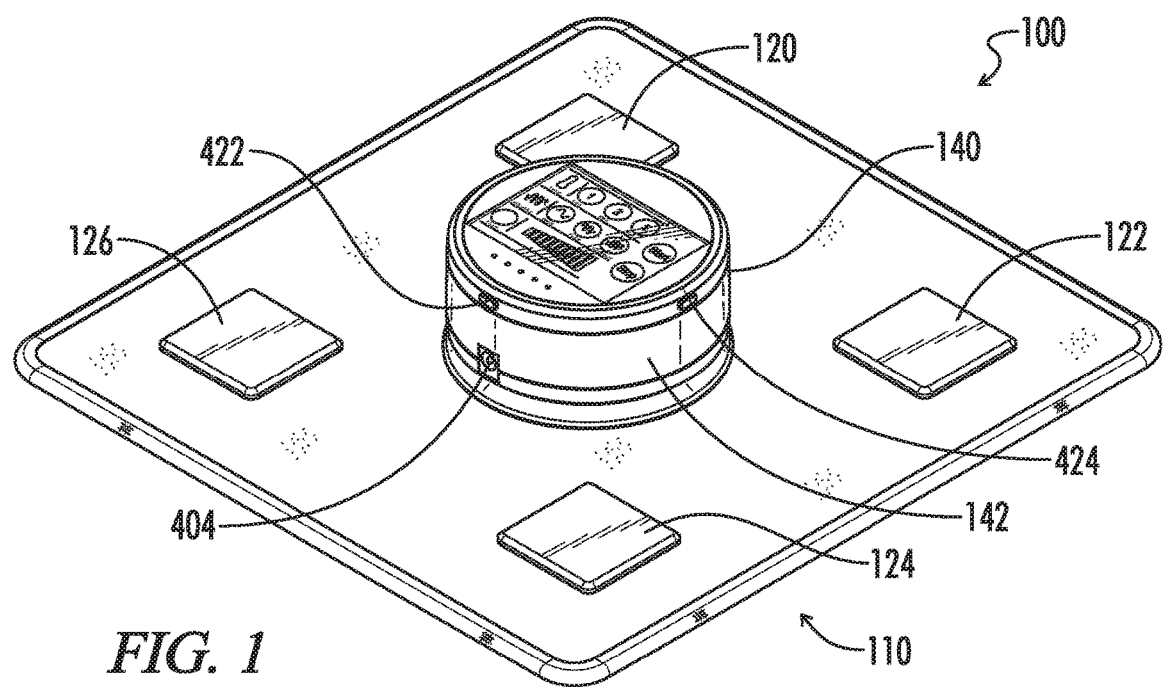
Figure 2:
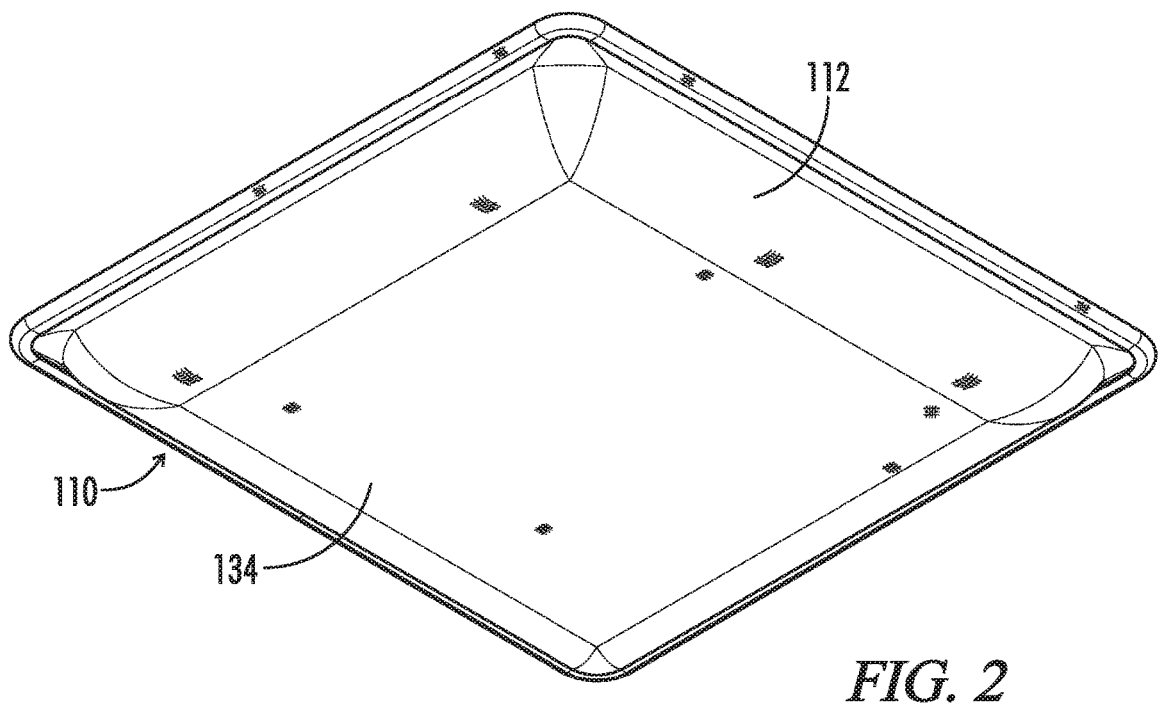
FIG. 2 illustrates a bottom perspective view of the vibration and heat generation apparatus of FIG. 1, the view showing the flexible bag-like lower housing extending from the upper flexible support structure of FIG. 1.
Figure 3:
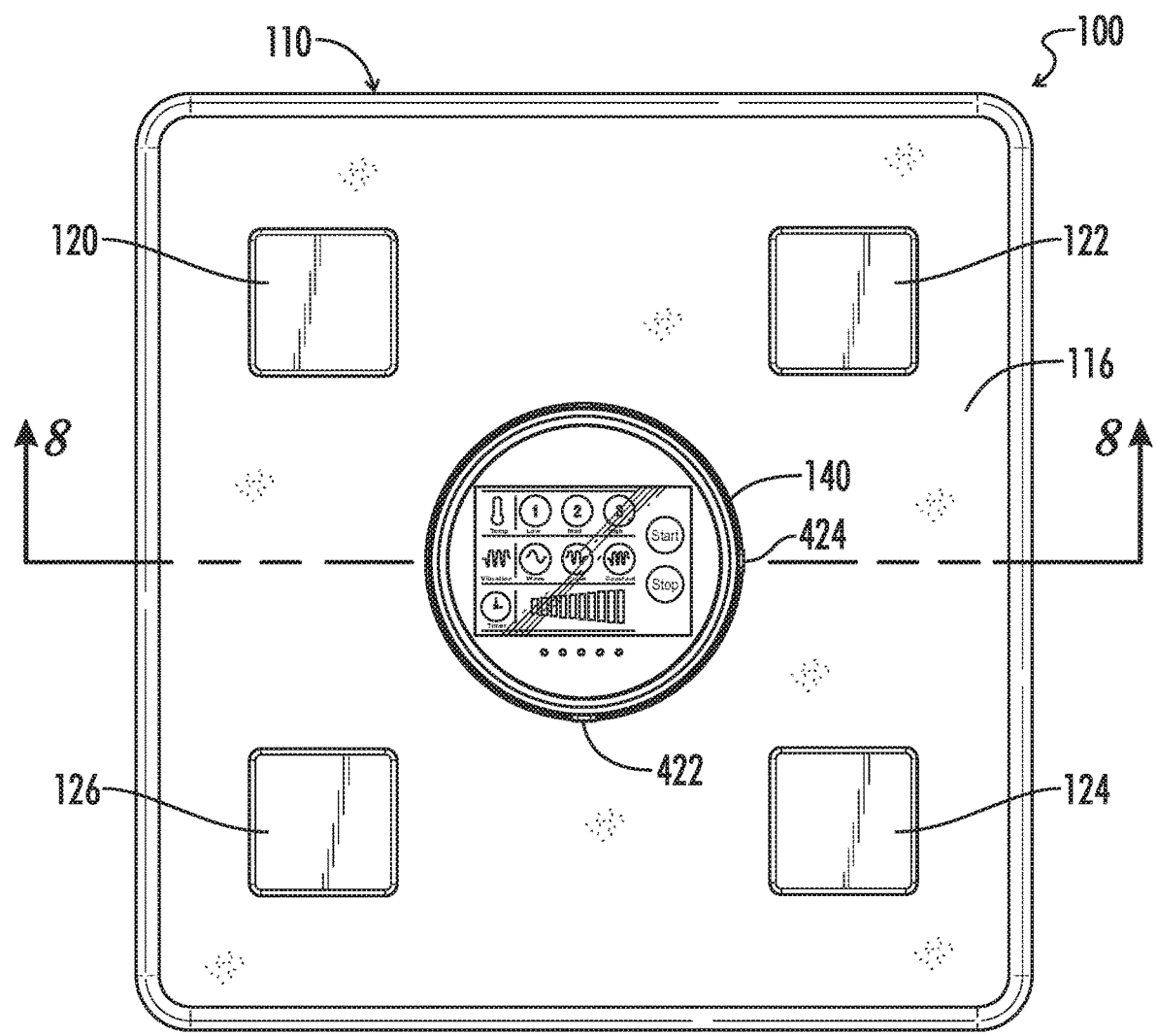
FIG. 3 illustrates a top plan view of the vibration and heat generation apparatus of FIG. 1.
Figure 4:
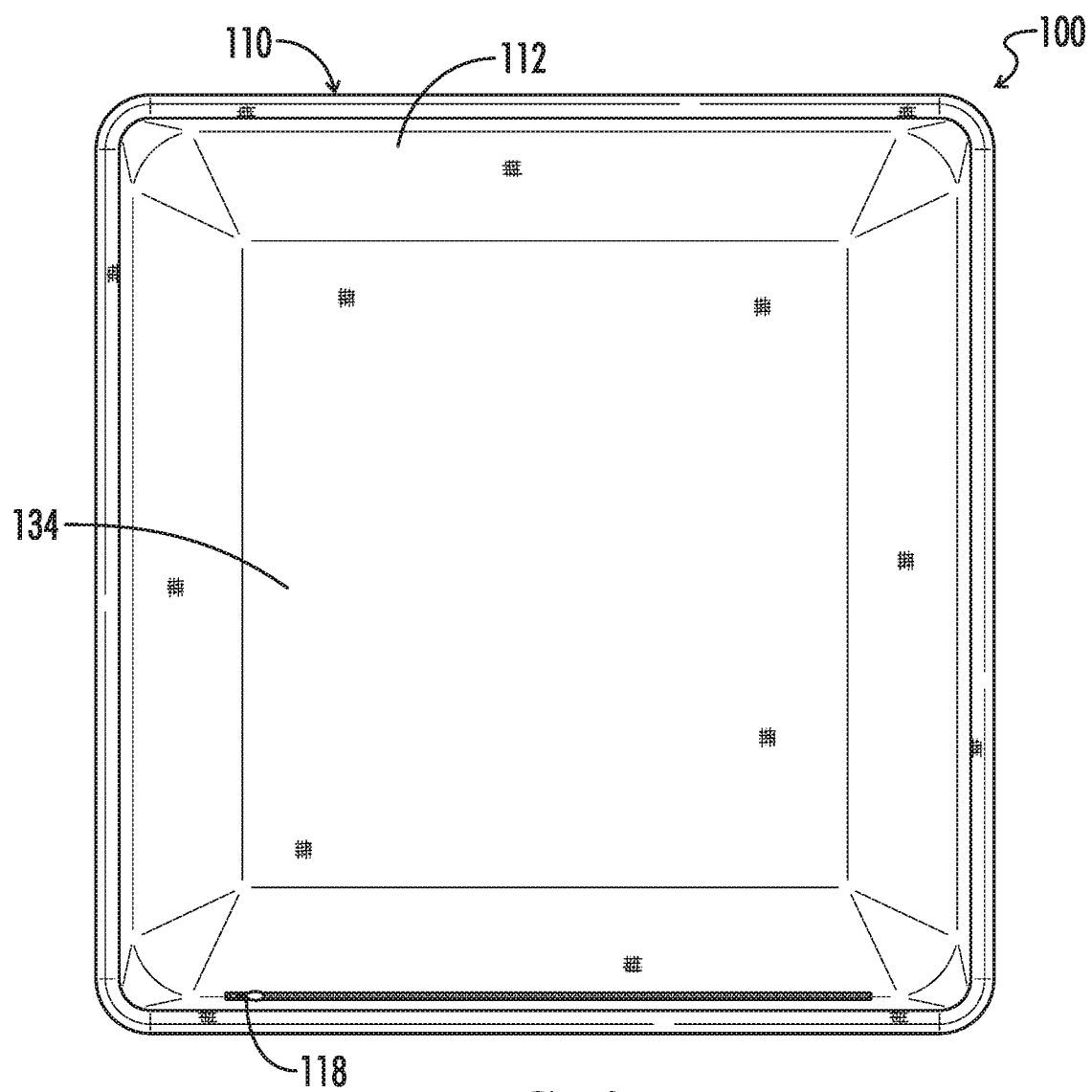
FIG. 4 illustrates a bottom plan view of the vibration and heat generation apparatus of FIG. 1.
Figure 5:
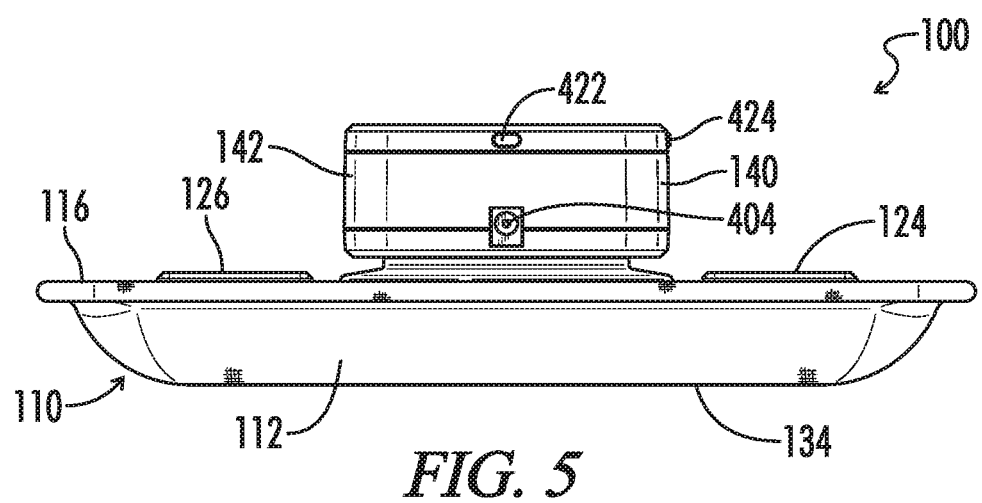
FIG. 5 illustrates a front elevational view of the vibration and heat generation apparatus of FIG. 1.
Figure 6:
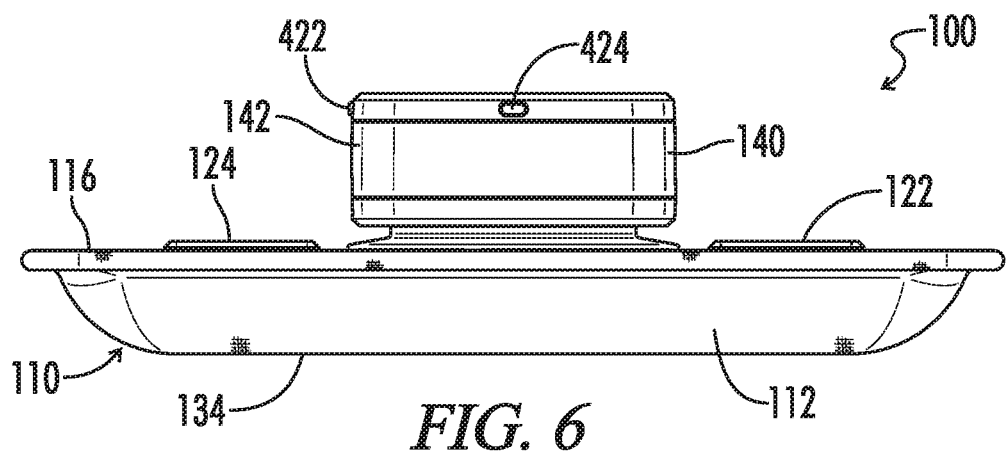
FIG. 6 illustrates a right side elevational view of the vibration and heat generation apparatus of FIG. 1.
Figure 7:
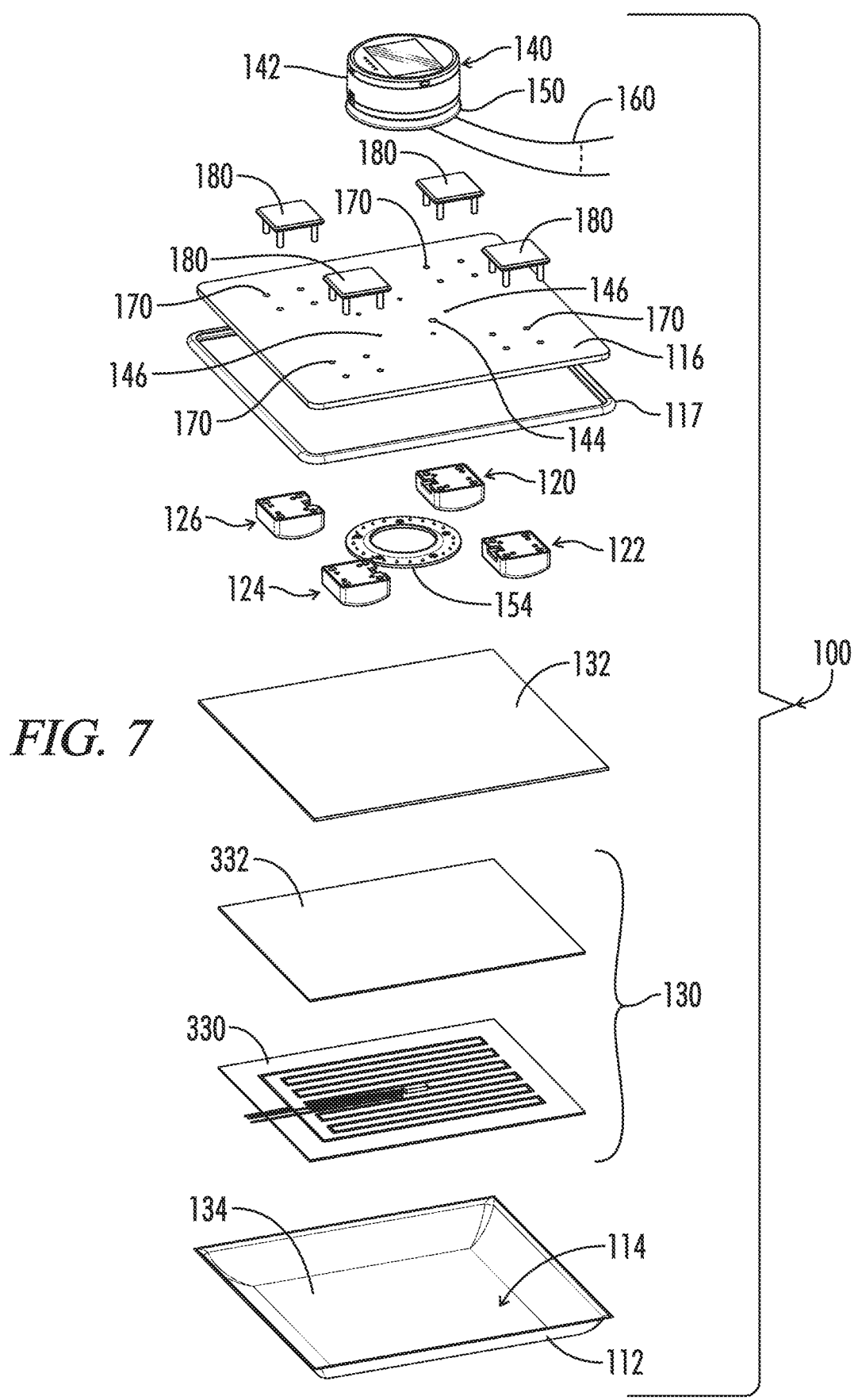
FIG. 7 illustrates an exploded perspective view of the vibration and heat generation apparatus of FIG. 1.

The vibration and heat generation apparatus 100 includes an enclosure 110. The enclosure comprises a lower bag-like structure 112 that houses an inner cavity 114 (FIG. 7). The lower bag-like structure is secured to an upper support structure 116 and extends distally from the upper support structure. In the illustrated embodiment, the lower bag-like structure comprises a strong elastomeric fabric such as, for example, a polyester-polyurethane copolymer fiber commonly referred to as spandex. In the illustrated embodiment, the upper support structure comprises a strong, flexible material. For example, the material may be an elastomeric material such as neoprene. Other strong, flexible materials can also be used. In the illustrated embodiment, the upper support structure has a width of approximately 10.25 inches (approximately 26.1 centimeters), a length of approximately 10.75 inches (approximately 27.3 centimeters) and a thickness of approximately 5 millimeters.

In the illustrated embodiment, the lower structure 112 is sewn to the upper support structure 116 along the four sides of the upper support structure. The seam between the two structures may be reinforced with bias tape 117 or other material as shown. In the illustrated embodiment, a zipper 118 is sewn into the lower structure to allow selective access to the cavity in the lower structure for initial installation of the components described below. The zipper is positioned near one edge of the lower structure as shown. The zipper is attached in such a manner that the edges of the fabric of the lower structure proximate to the two sides of the zipper are almost touching to substantially hide the underlying zipper from view. The material comprising the lower structure has generally rectangular dimensions sufficiently larger than the corresponding dimensions of the upper support structure such that the lower structure forms the inner cavity 114 with a sufficient depth relative to the upper support structure to accommodate a plurality of vibration elements (e.g., a first vibration pod 120, a second vibration pod 122, a third vibration pod 124 and a fourth vibration pod 126). The inner cavity further accommodates at least one heat generation unit 130. The heat generator is mechanically and thermally buffered from the vibration pods by a layer 132 of flexible foam.

As used herein, "bag-like structure" refers to various shapes the lower structure 112 may have when in use because the lower structure comprises a fabric material that is readily deformable to conform the material to irregular shapes. When the lower structure and the upper support structure 116 are resting on a flat surface, the lower structure has a selected general shape defined by its outer dimensions such that a flexible distal (e.g., lowermost in the illustrated orientation) wall 134 of the lower structure is generally parallel to the upper support structure. The actual shape of the lower structure varies in response to the current shape of the upper support structure. For example, when the outer edges of the upper support structure are bent downward, the distal wall of the lower structure may sag away from the upper support structure. On the other hand, when the upper support structure is positioned on a person's knee or other curved body part, the flexible distal wall of the lower structure easily deforms to conform to the irregular curvature of the body part.

A control unit 140 extends proximally (e.g., upward in the illustrated orientation) from a proximal (top) surface of the upper support structure 116. The control unit is housed within a generally cylindrical enclosure 142. As shown in the exploded view (FIG. 7), the upper support structure includes a though bore 144 that is positioned close to the center of the upper support structure. The through bore has a sufficient size to accommodate a plurality of power wires (e.g., twelve wires), which are discussed below. For example, the through bore may have a diameter between 0.1 inch and 0.25 inch. The control unit together with the enclosure 110, comprising the upper support structure and the lower structure 112, results in the vibration and heat generation apparatus 100 having an overall size and shape resembling a conventional flattened ice bag.

As shown in FIG. 7, the through bore 144 in the upper support structure 116 is surrounded by a plurality of mounting holes 146 formed through the upper support structure. For example, five mounting holes are equally spaced about a circle centered at the center of the upper support structure. In one embodiment, the circle has a diameter of approximately 3.05 inches. The cylindrical enclosure has an annular lower flange 150 that is positioned concentrically with respect to the cylindrical bore. The lower flange includes a plurality of threaded bores (e.g., five bores) 152 (FIG. 16) that are aligned with the mounting holes in the upper support structure. An annular compression flange 154 is mounted below the upper support structure. The compression flange includes a corresponding plurality of unthreaded bores (e.g., five bores) 156 (FIGS. 15 and 16) aligned with the mounting holes and aligned with the threaded bores of the annular lower flange. A corresponding plurality of screws (not shown) pass through the unthreaded bores of the compression flange and engage the threaded bores of the lower flange. As the screws are tightened, an annular portion of the upper mounting surface surrounding the central cylindrical bore is squeezed between the compression flange and the lower flange to secure the cylindrical enclosure to the upper support structure. It should be understood that the screws may be machine screws that engage pre-threaded bores in the lower flange or may be self-threading screws that create threads in the bores of the lower flange when the compression flange and the lower flange are first interconnected.

Figure 8:
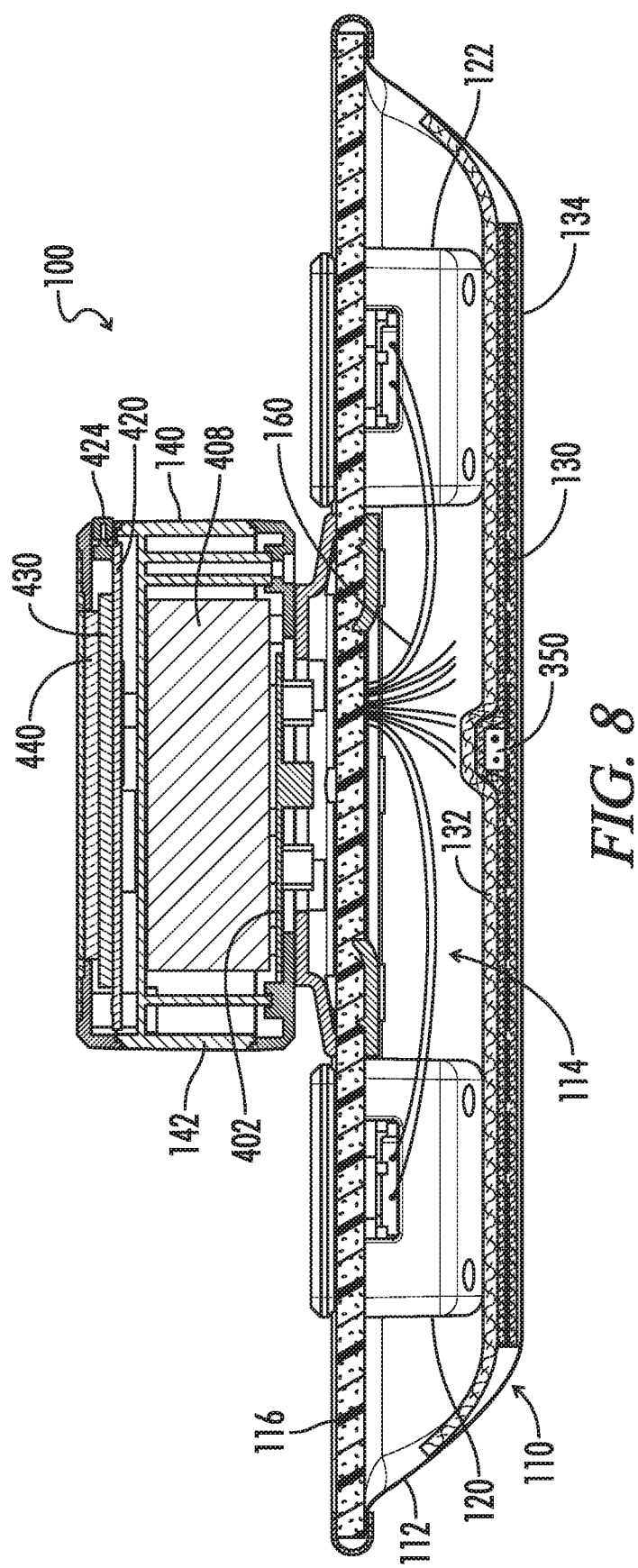
FIG. 8 illustrates a front elevational cross-sectional view of the vibration and heat generation apparatus of FIG. 1 taken along the line 8-8 in FIG. 3.

As further shown in FIG. 8, a plurality of electrical wires 160 extend from the lower portion of the cylindrical enclosure 142 of the control unit 140 and through the through bore 144 (FIG. 7) of the upper support structure 116. Additional structural and operational features of the control unit are described below.

The upper support structure 116 further includes a plurality of pod mounting bores 170 that extend through the upper support structure. In the illustrated embodiment, the upper support structure includes four sets of pod mounting bores. Each set of mounting bores comprises four bores arranged in a generally square pattern with a respective bore at the vertex of the square pattern. For example, in one embodiment, the bores in each set of positioned approximately 30 millimeters (approximately 1.2 inches) apart and have diameters of approximately 5 millimeters (approximately 0.2 inch). In the illustrated embodiment, each set of pod mounting bores is centered at selected distances from the center of the upper support structure. For example, the center of a rear left set is positioned approximately 2.85 inches to the left of the center of the upper support structure and approximately 2.85 inches toward the rear relative to the center of the upper support structure. In the illustrated embodiment, the sets of pod mounting bores are positioned substantially symmetrically with respect to the center of the upper support structure such that the center of each set is approximately the same distance from the center of the upper support structure. In other embodiments, the sets of mounting bores may be positioned differently from front to rear than from left to right, particularly if the upper support structure has a non-square upper surface. Note that as used herein, left and right, front and rear, and top and bottom are used to indicate positions relative to the drawings with the exposed upper surface of the upper support structure designated as the "top" or "proximal" surface. The apparatus may be used in many different orientations wherein the upper surface of the upper support structure may be oriented outward, downward or the like.

Figure 9:
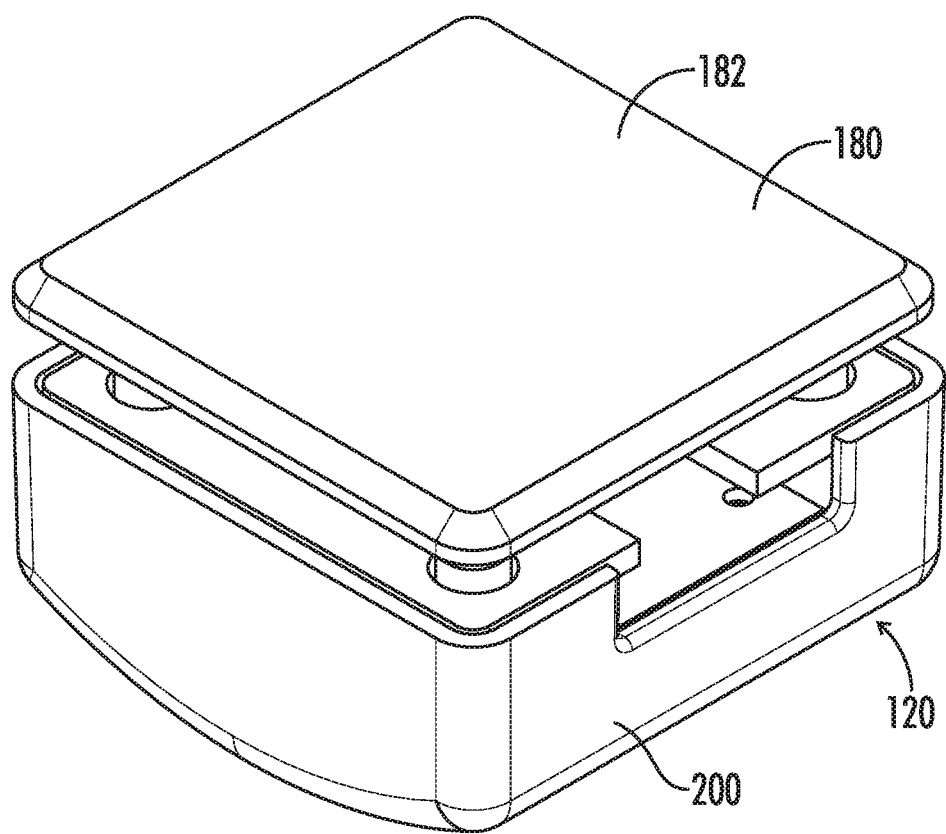
FIG. 9 illustrates an upper perspective view of one of the four vibrational pods of the vibration and heat generation apparatus of FIG. 1.
Figure 10:
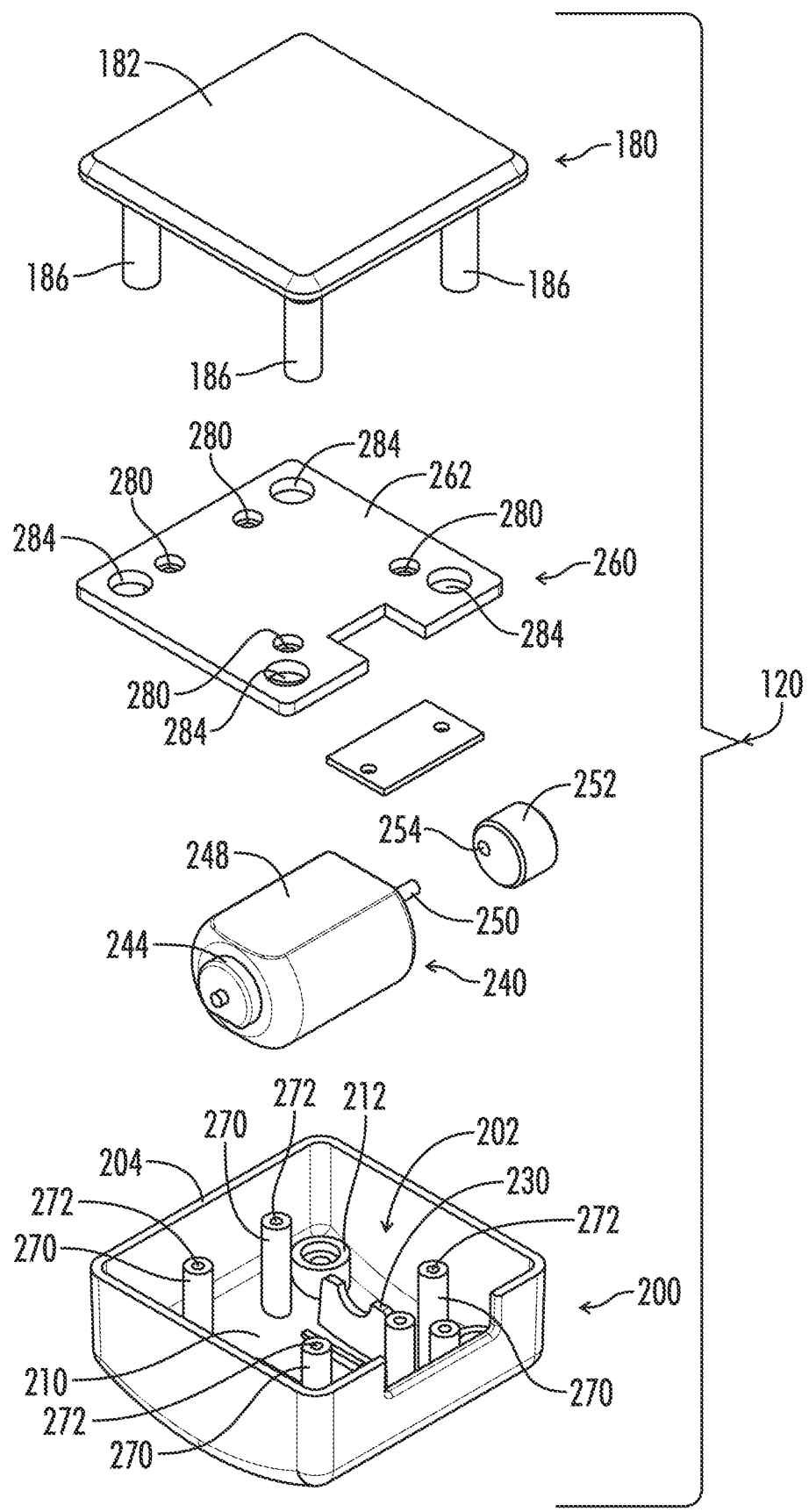
FIG. 10 illustrates an exploded perspective view of the vibrational pod of FIG. 9 showing the upper surfaces of the components.
Figure 11:
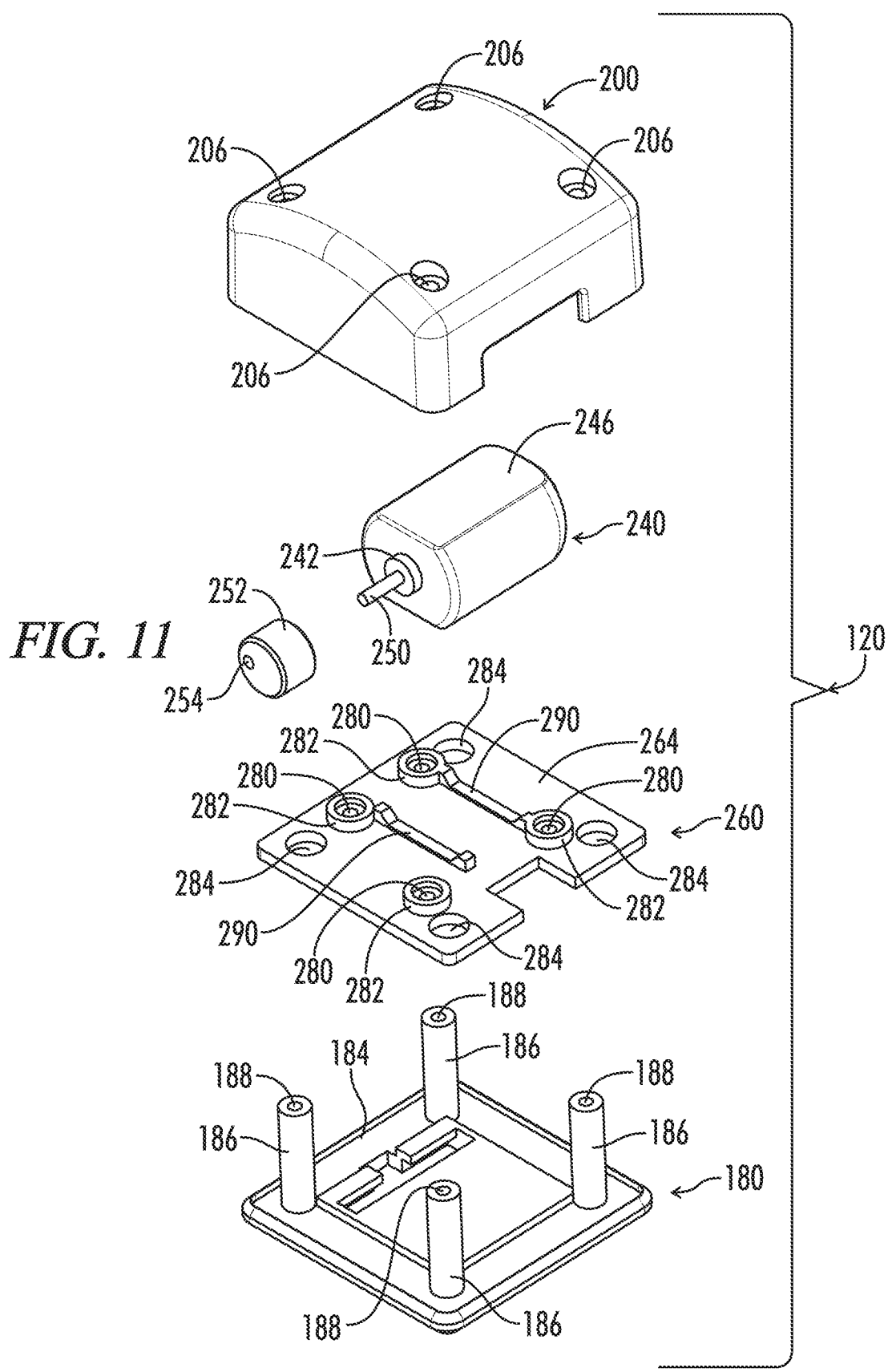
FIG. 11 illustrates an exploded perspective view of the vibrational pod of FIG. 9 with the view of FIG. 10 inverted to show the lower surfaces of the components.

The first vibration pod 120 is shown in more detail in FIGS. 9-11. The other three vibration pods 122, 124, 126 are identical or are substantially identical. The first vibration pod includes an upper cover 180. In the illustrated embodiment, a top surface 182 of the upper cover is square or substantially square with each side of the square having a length of approximately 45 millimeters). The upper cover has a thickness of approximately 4.25 millimeters to a lower surface 184. Four protrusions 186 extend from the lower surface of the upper cover. Each protrusion has a diameter selected such that each protrusion fits through a selected one of the mounting bores 170 in the rear left set of mounting bores. For example, in the illustrated embodiment, the protrusions have a diameter of approximately 5 millimeters. Each protrusion has a length of approximately 16.5 millimeters. The end of each protrusion opposite the top of the upper cover has a central bore 188 that may be threaded to receive a machine screw (not shown). Alternatively, the central bore may be threadable to receive a self-taping screw.

The first vibration pod 120 includes a lower cover 200 having a central cavity 202. The lower cover has a generally square upper surface 204 surrounding the central cavity. In the illustrated embodiment, the peripheral dimensions of the upper surface of the lower cover generally correspond to the peripheral dimensions of the upper cover 180. The lower cover has an arcuate lower surface having four through bores 206 formed therein. The through bores are spaced apart by distances corresponding to the spacing of the protrusions 186 of the upper cover 180. The through bores are counterbored with respect to the lower cover to receive the heads of the screws (not shown) that secure the lower cover to the upper cover.

A lower inner surface 210 of the lower cover 200 corresponds to the lower surface of the central cavity 202. Each of the through bores 206 is surrounded by a respective inner protrusion 212 that extends from the lower inner surface of the central cavity. The top surface of each inner protrusion has a respective counterbore 214 that surrounds the through bore and extends a selected distance into the protrusion. The diameter of each counterbore is selected to correspond to the outer diameter of the protrusions 186 extending from the top cover 180 (e.g., approximately 5 millimeters in the illustrated embodiment) so that each protrusion of the top cover fits snugly into the respective counterbore of one of the inner protrusions of the lower cover. The depth of the counterbore in each inner protrusion in the central cavity is selected such that when the protrusions of the top cover are engaged with the counterbores, the lower surface 184 of the top cover is spaced apart from the upper surface 204 of the bottom cover by a distance less than the thickness of the upper support structure 116. For example, in the illustrated embodiment, the two surfaces are spaced apart by approximately 1.85 millimeters, which is substantially less than the thickness (e.g., approximately 5 millimeters) of the upper support structure. Thus, when the top cover is secured to the bottom cover by the four screws (not shown) passing through the through bores 206 of the lower cover and engaging the central bores 188 of protrusions extending from the upper cover, the portions of the upper support structure in contact with the upper cover and the lower cover are squeezed between the two covers to secure the first vibration pod 120 to the upper support structure. The other three vibration pods 122, 124, 126 are secured to the upper support structure in a like manner.

The lower inner surface 210 of the lower cover 200 includes a first motor bearing support 230 and a second motor bearing support 232. Each motor bearing support is sized and positioned to receive a respective motor bearing as described below. The lower inner surface further includes three raised ribs 234 positioned between the first and second bearing supports. Each rib has a respective upper surface positioned a selected distance from the lower inner surface.

The first bearing support 230 includes a generally semicircular upper surface sized to receive a front bearing 242 of a motor 240. The second bearing support 232 includes a generally semicircular upper surface sized to receive a rear bearing 244 of the motor. The motor has a generally horizontal lower surface 246 that rests on the three raised ribs 234 when the bearings of the motor are positioned in the respective bearing supports. The motor also has a generally horizontal upper surface 248, which is parallel to the upper surface in the illustrated embodiment. The motor includes a shaft 250. A front portion of the shaft extends from the front bearing to support an eccentric mass 252. The eccentric mass is positioned within an unobstructed portion of the inner cavity and is able to move freely within the portion of the cavity when the shaft of the motor is rotated.

The lower cover 200 further includes a motor clamp plate 260 having an upper surface 262 and a lower surface 264. The motor clamp plate rests upon four clamp plate support protrusions 270 that extend upward from the lower inner surface 210. Each clamp plate support protrusion has a respective central bore 272. Each central bore may be threaded to receive the threads of a machine screw (not shown). Alternatively, each central bore may be threadable by a self-tapping screw.

The motor clamp plate 260 is sized to fit within the lower cover 200 and to rest upon the clamp plate support protrusions 270. The motor clamp plate includes four plate mounting through bores 280 that are aligned with the central bores of the clamp plate support protrusions. Each plate mounting through bore is counterbored on the upper surface 262 of the motor clamp plate so that the heads of the machine (or self-tapping) screws (not shown) do not extend above the upper surface of the motor clamp plate.

The lower surface 264 of the motor clamp plate 260 includes a respective protrusion 282 surrounding each plate mounting through bore 280. Each protrusion extends a short distance (e.g., approximately 2 millimeters; approximately 0.08 inch) below the lower surface. Each protrusion is counterbored to have an inside diameter corresponding to the outside diameter of a clamp plate support protrusion 270 (e.g., approximately 2.3 millimeters; approximately 0.09 inch in the illustrated embodiment). Thus, when the motor clamp plate is secured to the clamp plate protrusions, the motor clamp plate cannot shift laterally with respect to the lower cover.

The motor clamp plate 260 further includes four clearance through bores 284, which are positioned and sized to provide clearance for the four protrusions 186 that extend from the lower surface 184 of the upper cover 180. For example, in the illustrated embodiment, the clearance through bores have diameters of slightly greater than approximately 5 millimeters (approximately 0.2 inch) to provide a snug fit with respect to the protrusions.

The motor clamp plate 260 includes two motor engagement ribs 290 that extend from the lower surface 264. The engagement ribs are positioned to engage the generally horizontal upper surface 248 of the motor 240 when the motor clamp plate is positioned on the lower cover 200 of the first vibration pod 120. The thickness of each rib with respect to the lower surface of the motor clamp plate is selected such that when the motor clamp plate is fully secured by the four screws (not shown), the ribs are pressed against the horizontal upper surface of the motor. Accordingly, the motor is tightly secured between the ribs of the motor clamp plate and the three raised ribs 234 of the lower inner surface 210 of the lower cover 200.

In the illustrated embodiment, the motor 240 comprises a permanent magnet DC motor operating at approximately 5,300 revolutions per minute (RPM) from a 12-volt DC supply. In one embodiment, the motor comprises an FC130 style motor, which is commercially available from a number of sources. The motor draws approximately 0.09 Amperes at the rated RPM.

The motor 240 and the eccentric mass 252 together have an overall length of approximately 38 millimeters. The motor has an overall diameter of approximately 20.2 millimeters and is flattened to space the lower surface 246 and the upper surface 248 apart by approximately 15.4 millimeters.

The eccentric mass 252 is substantially cylindrical. The eccentric mass has an overall diameter of approximately 10 millimeters, and has a length along the shaft of the motor of approximately 7 millimeters. In the illustrated embodiment, the mass comprises powdered metal (e.g., iron), which is compacted to have a mass (weight) of approximately 3.5 grams. The eccentric mass is mounted on the shaft 250 of the motor 240 via a shaft bore 254 having a diameter of approximately 2.1 millimeters. In the illustrated embodiment, the shaft bore is offset from the center of the eccentric mass by approximately 2.2 millimeters to cause the mass to impart a vibration. The vibration is communicated from the shaft of the motor and through the bearings 242, 244 to bearing supports 230, 232 to cause the lower cover 200 of the vibration pod 120 to vibrate.

Each of the four vibration pods 120, 122, 124, 126 are electrically connected to the control unit as described below.

Figure 14:
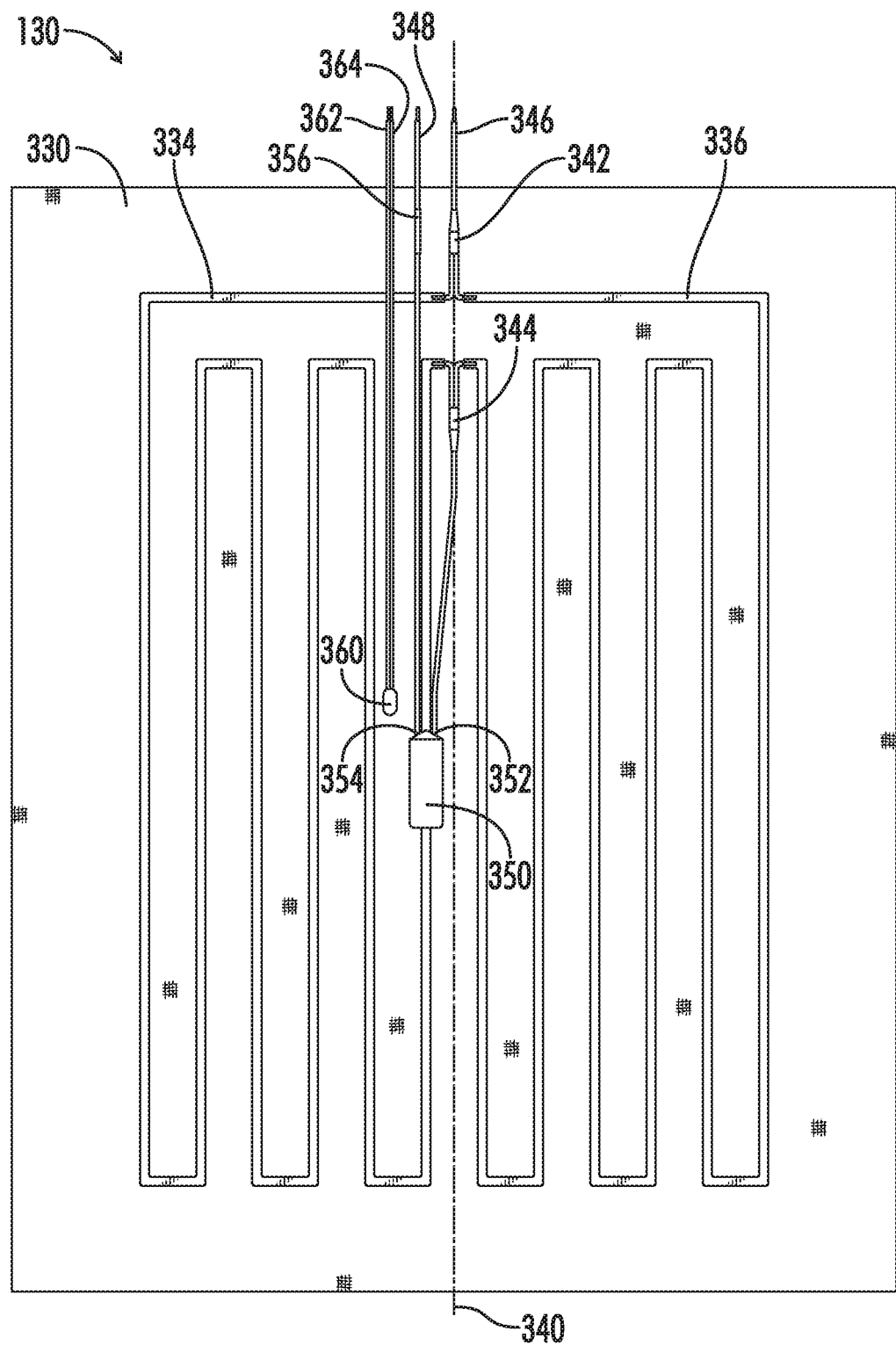
FIG. 14 illustrates a plan view of the electrical heating wire on the lower sheet of the heating pad of FIG. 13.

As illustrated in FIG. 14, in the illustrated embodiment, the heat generation unit 130 comprises a first (lower) rectangular sheet of cloth 330 and a second (upper) rectangular sheet of cloth 332. Each sheet has outer dimensions of approximately 250 millimeters by approximately 200 millimeters. In the illustrated embodiment, each sheet comprises a 200 g needle punch material (i.e., non-woven material formed by a conventional needle punching process) having a thickness of approximately 1.5 millimeters. The material has a density of approximately 200 grams per square meter. At least one electrical resistance wire is positioned between the two sheets. In the illustrated embodiment, a first resistance wire 334 and a second resistance wire 336 are secured to the upper surface of the lower sheet by lock stitching (not shown) in a conventional manner. The resistance wires can also be secured to the upper sheet in a similar manner. In one embodiment, each resistance wire comprises a thin, flat resistance wire, such as, for example, a commercially available titanium resistance wire. In the illustrated embodiment, the cross-sectional dimensions of the resistance wires are selected to provide a resistance of approximately 16 ohms per meter. Each resistance wire has a length of approximately 1.25 meters such that each wire has a total resistance of approximately 20 ohms.

The two resistance wires 334, 336 form two maze-like patterns, which are substantially symmetric about a centerline 340 of the lower sheet 330. Each resistance wire extends from a first common terminal 342 to a second common terminal 344 such that the two segments are connected in parallel. The first common terminal of the resistance wires is connected directly to a first supply wire 346. The second common terminal of the resistance wires is connected to a second supply wire 348 via a thermal cutoff switch 350. The thermal cutoff switch has a first terminal 352 connected to the second common terminal of the resistance wires and has a second terminal 354 connected to the second supply wire via a connector 356.

The thermal cutoff switch 350 is normally closed such that the control unit 140 is electrically connected to the second common terminal 344 of the resistance wires 334, 336. The first common terminal 342 of the resistance wires is always connected to the control unit. Thus, current is conducted from the first terminal around each of the first resistance wire and the second resistance wire in parallel. Since each resistance wire has a resistance of approximately 20 ohms, each resistance wire generates approximately 14 watts of heat at a voltage of approximately 16.8 volts. The two resistance wires generate a total of approximately 28 watts of heat.

The thermal cutoff switch 350 is set to open the circuit when the temperature proximate to the thermal cutoff switch exceeds approximately 80 degrees Celsius +/−5 degrees and to stay open until the temperature reduces to approximately 55 degrees Celsius +/−10 degrees. In one embodiment, the thermal cutoff switch comprises a KLS-KSD9700 thermal fuse commercially available from Ningbo KLS Imp & Exp Co. Ltd. In Beilun Ningbo Zhejiang China. The thermal cutoff switch is positioned across portions of the heating wire such that the thermal cutoff switch directly senses the temperature of the heating wire and disconnects the electrical path well before the heat from the heating wire is communicated though the lower sheet and the material of the lower structure 112 to a user (not shown).

Figure 15:
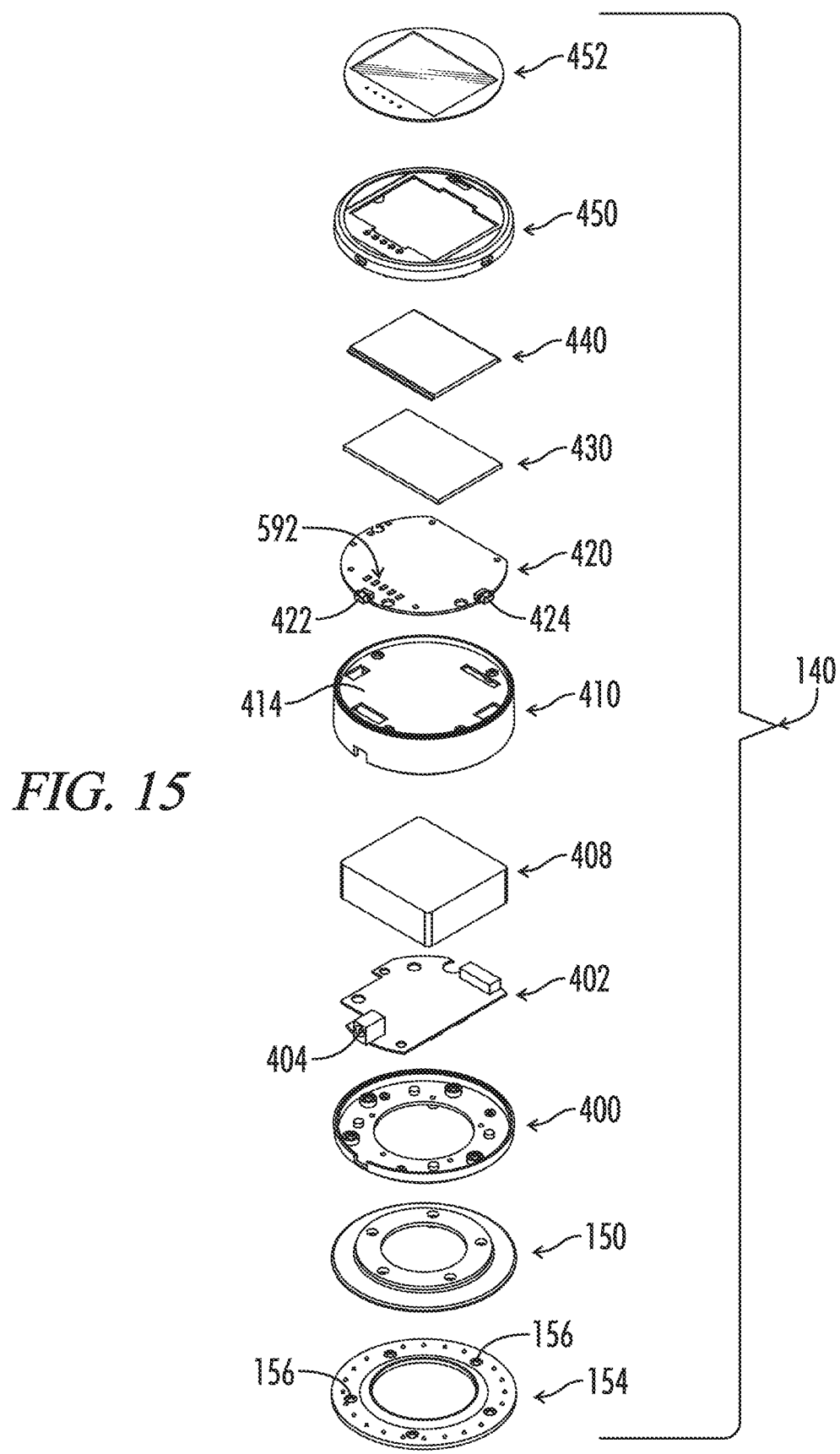
FIG. 15 illustrates an exploded upper perspective view of the cylindrical control unit of the vibration and heat generation apparatus.

As further shown in FIGS. 14 and 15, a thermistor 360 is secured to the first (lower) sheet of cloth 330. The thermistor is also positioned near the center of the first sheet; however, the thermistor is positioned between two adjacent segments of the first resistance wire 334 rather than directly on the resistance wire. A first wire 362 and a second wire 364 extend from the thermistor and are connected to the control unit 140. In one embodiment, the thermistor is a negative temperature coefficient (NTC) thermistor. For example, the thermistor may be an MF52-104F-3950-600L thermistor commercially available from Dongguan Xinxiang Electronic Technology Co., Ltd., in China. The thermistor has a resistance that varies over a wide temperature range. For example, at 55 degrees Celsius, the thermistor has a resistance of approximately 29,733 ohms; at 60 degrees Celsius, the thermistor has a resistance of approximately 24,753 ohms; and at 71 degrees Celsius, the thermistor has a resistance of approximately 16,794 ohms. The resistance of the thermistor is readily detectable in a conventional manner to determine when the temperature of the thermistor exceeds a selected temperature.

After the thermal cutoff switch 350 and the thermistor 360 are positioned on the first (lower) sheet 330, and after the first common terminal 342 is connected to the first supply wire 346 and the second common terminal 344 is connected to a second supply wire 348, the second (upper) sheet 332 is secured to the first sheet. In the illustrated embodiment, the lower surface of the second sheet includes an adhesive to removably attach the second sheet to the first sheet.

As further shown in FIGS. 7 and 8, the layer 132 of flexible foam is positioned above the second (upper) sheet 332 between the second sheet and the vibration pods 120, 122, 124, 126 to partially buffer the vibrations provided by the vibration pods when operated as described below.

Figure 16:
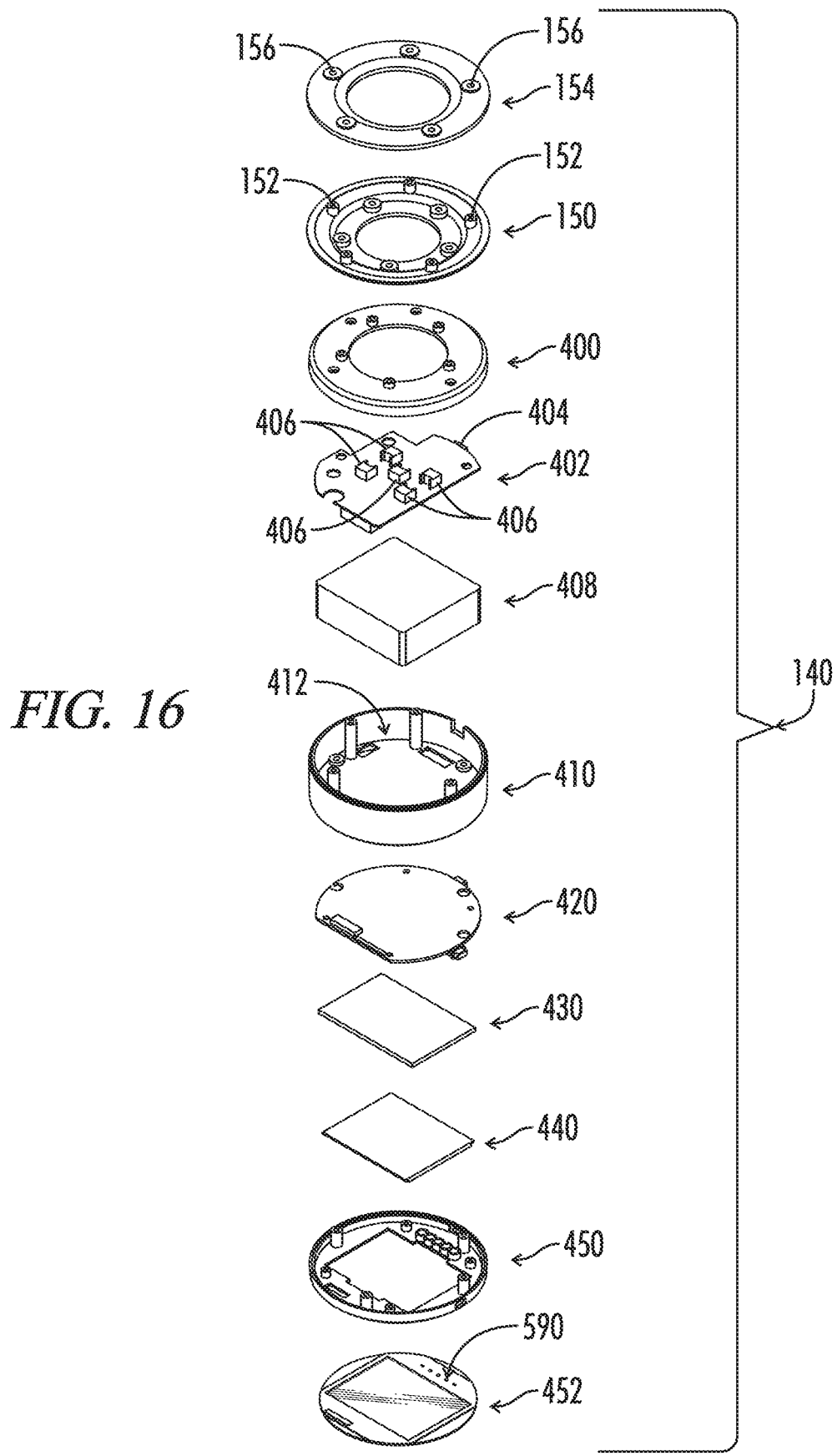
FIG. 16 illustrates an exploded perspective view of the cylindrical control unit of FIG. 15 with the view of FIG. 15 inverted to show the lower surfaces of the components of the control unit.

The structure of the control unit 140 is shown in more detail in FIGS. 15 and 16. As described above, the control unit includes the lower flange 150 and the removably attachable annular compression flange 154. The lower flange is connected to a lower body portion 400 of the control unit. The lower body portion supports a first printed circuit board (PCB) 402.

The first PCB 402 includes an electrically and mechanically attached conventional charging jack 404, which extends through a notch in the wall of the lower body portion. The first PCB also includes a plurality of metal oxide semiconductor field effect transistors (MOSFETs) (not shown) that provide power to the vibration pods 120, 122, 124, 126 and to the heat generation unit 130 via a plurality of connectors 406. A lithium polymer (LiPo) battery 408 rests upon the first PCB and is electrically connected to the first PCB to receive charging energy via the first PCB and to provide operational energy to the other components of the control unit. The lower body portion includes a central opening to allow wiring from the connectors to the vibration pods 120, 122, 124, 126 and to the heat generation unit 130 to pass therethrough.

A cylindrical middle body portion 410 is positioned over the first PCB 402 and the LiPo battery 408 and is secured to the lower body portion. A lower end 412 of the middle body portion is open. An upper end 414 of the middle body portion is generally closed; however, the upper end includes a plurality of through passages to allow wiring to pass through the upper end from the first PCB to a second PCB 420. The middle body portion also includes a notch to accommodate the charging jack 404.

The second PCB 420 rests on the upper end 414 of the middle body portion 410 and is secured to the upper end by suitable fasteners (not shown). The second PCB is electrically connected to the first PCB 402 via a plurality of wires (not shown). The second PCB receives power from the battery 406 via the first PCB 402. The second PCB also receives input power from the power input jack 404. The second PCB generates a battery charging voltage of approximately 16.8 volts, which is provided to the battery via the first PCB. The second PCB also generates a motor voltage of approximately 12 volts, which is provided to the first PCB as a motor driving voltage. The second PCB generates control signals to control the power applied to the vibration pods 120, 122, 124, 126 and to the heat generation unit 130. The control signals are applied to the MOSFETs (not shown) on the first PCB.

The second PCB 420 communicates with a liquid crystal display (LCD) panel and a touch panel (described below). The second PCB is electrically connected to a first pushbutton switch 422 and to a second pushbutton switch 424. The two switches are mounted on the printed circuit board in the illustrated embodiment. The first pushbutton switch is manually operable to turn the vibration and heat generation apparatus 100 on and off. The second pushbutton switch is manually operable to select between two brightness levels for the LCD display. Each brightness level corresponds to a respective operational mode for the touch panel. The electronic circuitry on the second PCB and the two operational modes are described in more detail below.

An LCD panel 430 is positioned proximate to and electrically connected to the second PCB 420. For example, the LCD panel may be a "daughter board" mechanically connected to the second PCB via a connector (not shown). The LCD panel may also be connected to the second PCB via a plurality of electrical wires (not shown). The LCD panel is responsive to signals from the second PCB to generate signals to cause images to be displayed as described below.

A generally transparent touch panel 440 is positioned over the LCD panel 430. The touch panel generates signals resulting from manual manipulation of selected portions of the touch panel. The signals are provided to the second PCB. In certain embodiments, the LCD panel and the touch panel are provided in combination as a single integrated package. Such combinations are commercially available and are well understood. In the illustrated embodiment, the LCD panel and the display panel comprise a Model No. YH26167VNT display commercially available from Dongguan Quinniahong Electronic Technology Co., Ltd., in China.

An upper body portion 450 is positioned over the LCD panel 430, the touch panel 440 and the second PCB 420. A middle section of the upper body portion is removed to expose the LCD touch panel such that the images displayed on the LCD touch panel are visible to a user and such that a user can access the surface of the LCD touch panel with the user's fingertips or with a suitable stylus. In the illustrated embodiment, a bezel 452 is positioned over the upper body portion to frame the active portions of the LCD panel and the touch panel.

Figure 17:
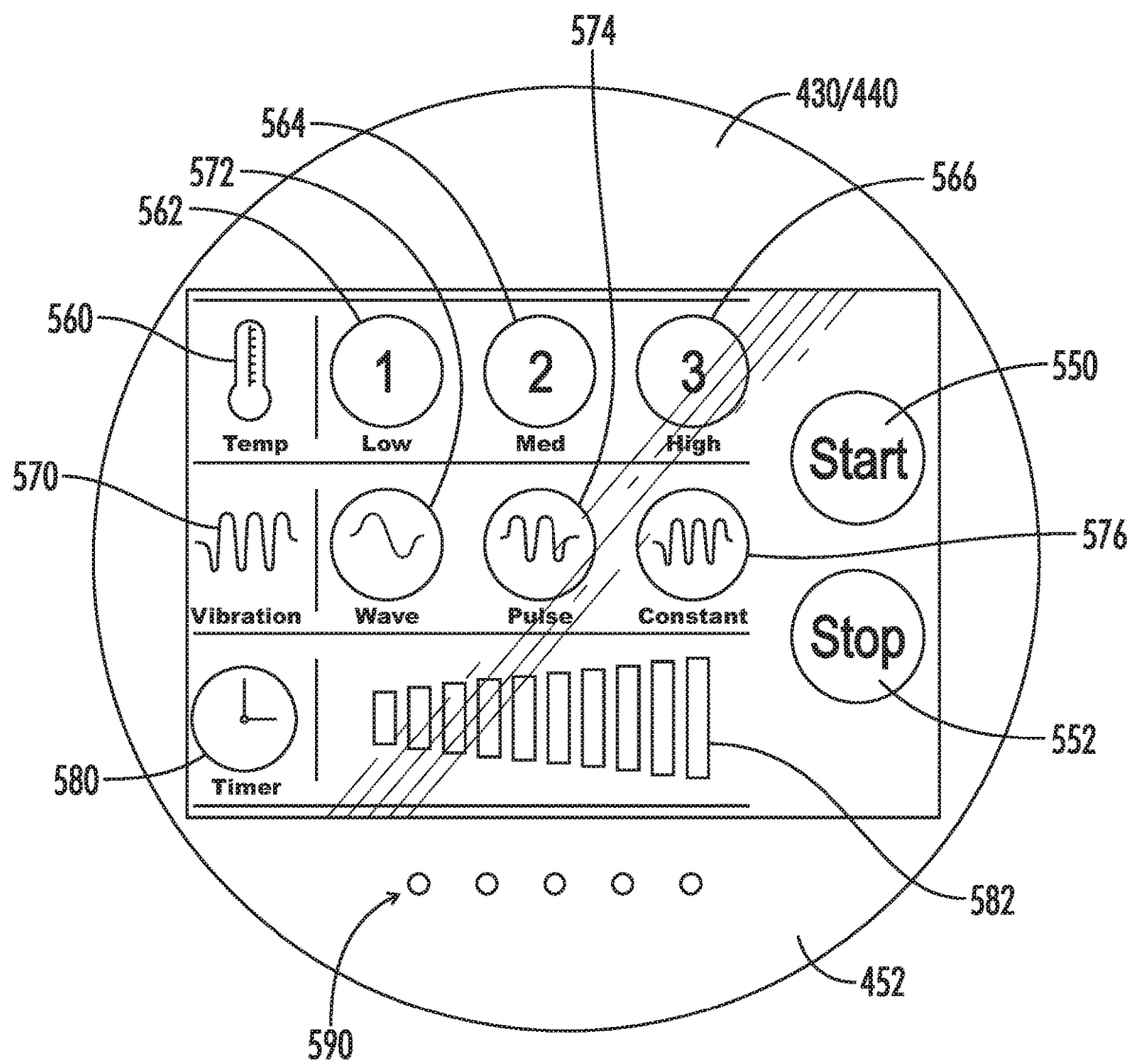
FIG. 17 illustrates a top plan view of the touch panel control interface positioned on the upper end of the cylindrical control unit of FIG. 16.

As shown in FIG. 17, the upper end of the control unit 140 comprises the LCD panel 430 and the overlying touch panel 440. The LCD panel displays a plurality of icons to convey information to a user regarding the operational mode of the vibration and heat generation apparatus 100 and to indicate to a user where to touch the touch panel to control the operation of the vibration and heat generation apparatus.

In the illustrated embodiment, a right hand portion of the LCD panel 430 displays a "Start" icon 550 and a "Stop" icon 552. Each icon represents a respective touch active portion of the overlying touch panel 440 such that touching the area of the "Start" icon activates the vibration and heat generation apparatus and touching the area of the "Stop" icon deactivates the vibration and heat generation apparatus. Although the vibration and heat generation apparatus is deactivated, the power remains on to provide an active display until the first pushbutton switch is pushed to turn off the power. When the Start icon is touched to activate the apparatus, the display brightens (temporarily) to indicate that the apparatus is active.

The LCD panel 430 further displays a temperature icon 560 (represented by a thermometer symbol and the underlying letters "Temp." Three temperature selection icons are aligned with the temperature icon. Each temperature selection icon corresponds to a touch active area of the overlying touch panel 440. A first temperature selection icon 562 is labeled with "1" and is further identified with "Low." A second temperature selection icon 564 is labeled with "2" and is further identified with "Med." A third temperature selection icon 564 is labeled with "3" and is further identified with High."

When the control unit 140 is first turned on and the start icon 550 is touched, no heating mode is selected. Touching the area of the first temperature selection icon 562 activates the "Low" heat mode icon and selects a temperature setting of approximately 42 degrees Celsius (approximately 108 degrees Fahrenheit). A ring around the first temperature selection icon is illuminated on the underlying LCD panel 430 to indicate that the low temperature range is selected. Touching the area of the first temperature selection icon when the ring is illuminated turns off the low heat mode.

Touching the area of the second temperature selection icon 564 activates the "Med" heat mode icon and selects a temperature setting of approximately 50 degrees Celsius (approximately 122 degrees Fahrenheit). A ring around the second temperature selection icon is illuminated on the underlying LCD panel 430 to indicate that the medium temperature range is selected. Touching the area of the second temperature selection icon when the ring is illuminated turns off the medium heat mode.

Touching the area of the third temperature selection icon 566 activates the "High" heat mode icon and selects a temperature setting of approximately 60 degrees Celsius (approximately 140 degrees Fahrenheit). A ring around the third temperature selection icon is illuminated on the underlying LCD panel 430 to indicate that the high temperature range is selected. Touching the area of the third temperature selection icon when the ring is illuminated turns off the high heat mode.

Touching the stop icon area of the touch panel 440 clears any selected temperature selection.

In operation, the control unit 140 monitors the resistance of the thermistor 360 and turns the heat generation unit 130 off and on based on the resistance. For example, when the "Low" heat setting is selected, the control unit detects when the thermistor becomes sufficiently hot (e.g., approximately 42 degrees Celsius) such that the resistance of the thermistor decreases below approximately 48,900 ohms. The control unit turns the heat generation unit off. The control unit continues to monitor the resistance of the thermistor while the thermistor cools and the resistance of the thermistor increases. When the thermistor is sufficiently cool (e.g., at a temperature below approximately 37 degrees Celsius) and the resistance of the thermistor increases above approximately 59,900 ohms, the heat generation unit is turned back on. The control unit operates in a similar manner for the other two temperature settings. For example, when the "Med" heat setting is selected, the control unit turns off the heat generation unit when the resistance of the thermistor decreases below approximately 35,900 ohms (corresponding to a temperature of approximately 50 degrees Celsius) and turns the heat generation unit back on when the resistance of the thermistor increases above approximately 48,900 ohms (corresponding to a temperature of approximately 42 degrees Celsius. When the "High" heat setting is selected, the control unit turns off the heat generation unit when the resistance of the thermistor decreases below approximately 24,750 ohms (corresponding to a temperature of approximately 60 degrees Celsius) and turns the heat generation unit back on when the resistance of the thermistor increases to above approximately 32,000 ohms (corresponding to a temperature below approximately 53 degrees Celsius).

The LCD panel 430 further displays a vibration selection icon 570 (represented by a waveform symbol and the underlying word "Vibration." Three vibration selection icons are aligned with the vibration icon. Each vibration selection icon corresponds to a touch active area of the overlying touch panel 440. A first vibration selection icon 572 is labeled with a first waveform icon and is further identified with "Wave." A second vibration selection icon 574 is labeled with a second waveform icon and is further identified with "Pulse." A third vibration selection icon 576 is labeled with a third waveform icon and is further identified with "Constant."

In the illustrated embodiment, when the control unit 140 is first turned on and the start icon 550 is touched, no vibration mode is selected. Touching the area of the first vibration selection icon 572 activates the wave vibration mode in which the four vibration pods 120, 122, 124, 126 are turned on in a selected sequence. A ring around the first vibration selection icon is illuminated on the underlying LCD panel 430 to indicate that the wave vibration mode is selected. In one embodiment, the selected sequence of the wave vibration mode comprises turning on the first vibration pod for approximately one-quarter second; then turning off the first vibration pod and turning on the second vibration pod for approximately one-quarter second; then turning off the second vibration pod and turning on the third vibration pod for approximately one-quarter second; then turning off the third vibration pod and turning on the fourth vibration pod for approximately one-quarter second. The next sequence is started by turning off the fourth vibration pod and turning on the first vibration pod for approximately one-quarter second and repeating the foregoing steps. Rather than repeating the same sequence, subsequent sequences may turn the vibration pods on and off in a different order. Multiple vibration pods may also be turned on at the same time. The sequence or sequences are repeated as long as the control unit remains in the wave vibration mode. Touching the area of the first vibration selection icon when the ring is illuminated turns off the wave vibration mode.

Touching the area of the second vibration selection icon 574 activates the pulse vibration mode icon 574. A ring around the second vibration selection icon is illuminated on the underlying LCD panel 430 to indicate that the pulse vibration mode is selected. In one embodiment, in the pulse vibration mode, the four vibration pods 120, 122, 124, 126 are turned on at the same time for a predetermined duration (e.g., approximately one-half second), and then turned off at the same time for a predetermined duration (e.g., approximately one-half second). The sequence of "all on" followed by "all off" is repeated as long as the control unit remains in the pulse vibration mode. Touching the area of the second vibration selection icon when the ring is illuminated turns off the pulse vibration mode.

Touching the area of the third vibration selection icon 576 activates the constant vibration mode icon 574. A ring around the third vibration selection icon is illuminated on the underlying LCD panel 430 to indicate that the constant vibration mode is selected. In one embodiment, the four vibration pods 120, 122, 124, 126 are operated continuously as long as the constant vibration mode is selected. Touching the area of the third vibration selection icon when the ring is illuminated turns off the constant vibration mode.

Touching the stop icon 552 turns off the currently selected temperature mode and the currently selected vibration mode.

Any of the three vibration modes can be selected in combination with any of the three heat modes. Furthermore, a vibration mode may be selected without selecting a heat mode; and a heat mode may be selected without selecting a vibration mode.

The display panel 430 further displays a timer icon 580 represented by a solid circle and the underlying word "Timer." The timer icon is aligned with a sequence of 10 vertical timer bar icons 582 with increasing heights. Each timer bar icon represents an amount of time for which the vibration and heating apparatus 100 operates at the current vibration mode and heat mode settings before turning off automatically. For example, each timer bar icon may represent 2 minutes of remaining time such that when all bars are active, approximately 20 minutes of time remains before the apparatus turns off automatically. The tallest (right-most) timer bar is turned off at the end of approximately 2 minutes to indicate that only approximately 18 minutes remain. Each timer bar is sequentially turned off in similar intervals until the shortest (left-most) timer bar is turned off and the overall operation of the vibration and heat generation apparatus is stopped. The area of the timer bars is touch active such that any portion of the area of the timer bars can be touched at any time to reset the timer to the full twenty minutes. The timer bars are deactivated by touching the "Stop" icon 552. Touching the "Start" icon 550 restarts the timer at 20 minutes (all timer bars illuminated).

Although not part of either the LCD panel 430 or the touch panel 440, a plurality of display ports 590 (e.g., five display ports) are formed in the bezel 450. The display ports are aligned with a corresponding plurality of light emitting diodes (LEDs) 592 on the second PCB 420. The five LEDs are selectively illuminated to indicate the current charge on the LiPo battery 408. For example, all five LEDs are illuminated to indicate a fully charged battery. One LED at a time is turned off as the charge of the battery decreases. The last illuminated LED may be illuminated in a different color (e.g., red versus green) to indicate that the battery needs to be recharged.

The control unit 140 further includes the first conventional pushbutton switch 422 located on the perimeter of the control unit just below the LCD display 430 and touch panel 440 and facing the front of the vibration and heat generation apparatus 100. The first pushbutton switch operates as a master on/off switch to enable a user to operate the switch to turn the vibration and heat generation apparatus off to conserve the energy stored in the battery. The user operates the first pushbutton switch to turn the vibration and heat generation apparatus on such that the LCD display and the touch panel are activated to respond to touch commands as described above. The control unit further includes the second conventional pushbutton switch 424 located on the perimeter of the control unit just below the LCD panel and the touch panel and facing the right of the vibration and heat generation apparatus. The second pushbutton switch provides a signal to the control unit to selectively dim the LCD panel to reduce energy consumption when full brightness is not required. The activation of the second pushbutton switch also disables the touch panel from being responsive to touching by a user. Thus, any inadvertent touching of the touch panel will not change the mode of operation of the vibration and heat generation apparatus. In the illustrated embodiment, the LCD panel is automatically dimmed and the touch panel is automatically disabled after a short period of no touching by the user. For example, the LCD panel is dimmed and the touch panel is disabled after approximately 5 seconds of no touching by the user.

Figure 18:
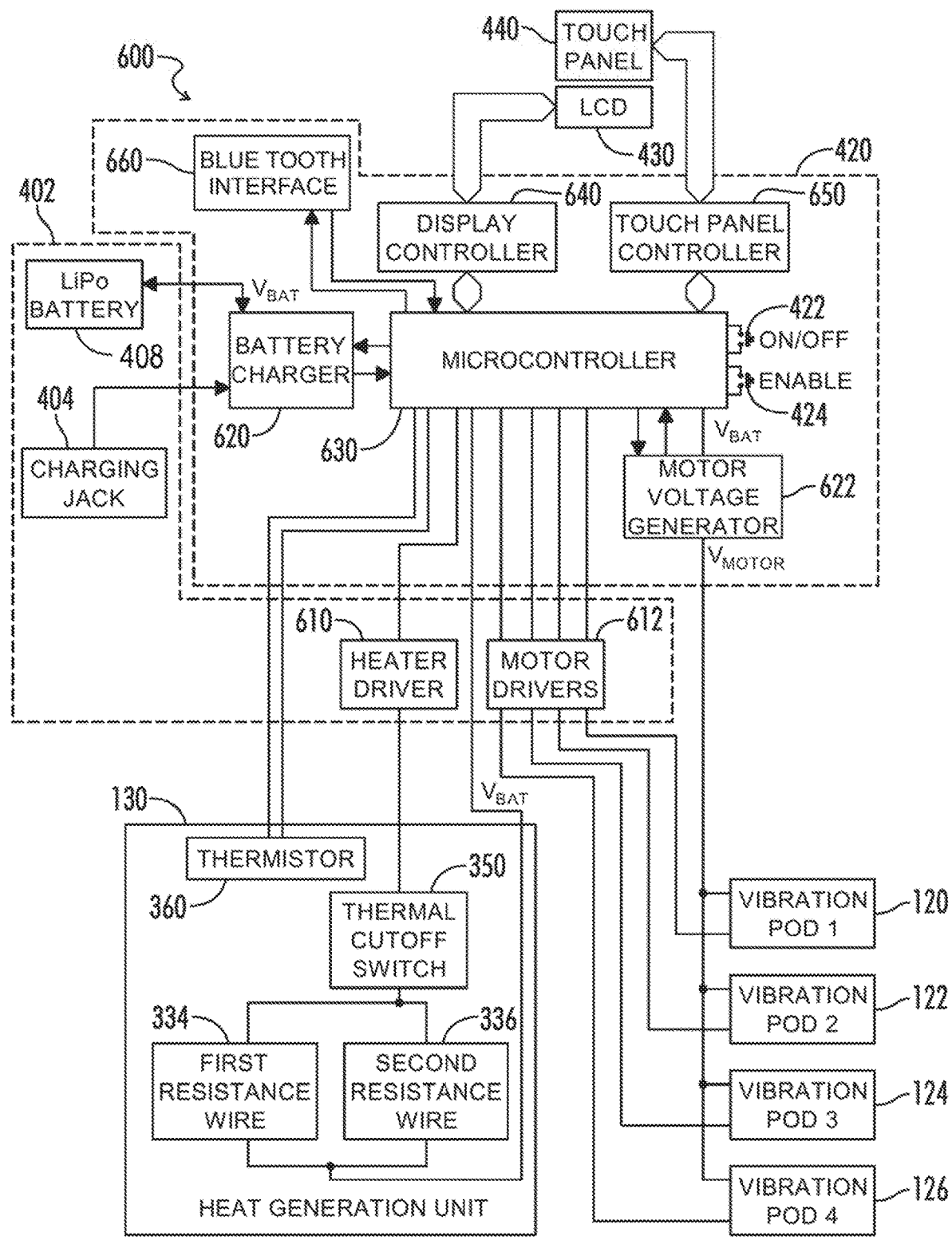
FIG. 18 illustrates a block diagram of the electrical and electronic circuitry of the vibration and heat generation apparatus of FIG. 1.

FIG. 18 illustrates a block diagram 600 of the electrical circuitry of the vibration and heat generation apparatus 100. In FIG. 18, previously identified components are numbered as before. The first PCB 402 and the second PCB 420 are illustrated in dashed lines to encompass the components on each PCB. The locations of the various components can vary in other embodiments. For example, the LiPo battery 408 and the charging jack 404 are shown as being part of the first PCB as described above. In the illustrated embodiment, the first PCB includes a heater driver 610 and motor drivers 612. In the illustrated embodiment, the heater driver and each of the four motor drivers comprises a power MOSFET that provides a current return path to ground when the respective driver is activated. In the illustrated embodiment, the battery LiPo battery is charged by a battery charger circuit 620, which is located on the second PCB. The battery charger circuit receives power from a conventional wall adapter (not shown) and charges the LiPo battery to approximately 16.8 volts. A second power control circuit ("motor voltage generator") 622 converts the battery voltage to approximately volts to drive the vibration motors 120, 122, 124, 126. In the illustrated embodiment, the motor voltage generator is also located on the second PCB. Although not shown in FIG. 18, the second PCB also includes circuitry to convert the battery voltage a supply voltage for the digital electronics circuitry. For example, a conventional 5-volt three-terminal voltage regulator (e.g., a Holtek HT7550-1) is suitable.

The second PCB 420 includes a microcontroller 630 that controls the operation of the other components on the second PCB and the first PCB 402. For example, the microcontroller in the illustrated embodiment is a commercially available 44-pin microcontroller that runs a conventional 8051 instruction set. One such microcontroller is an SN8F5707 microcontroller from Sonix in Taiwan. The microcontroller generates control signals to and receives feedback signals from the battery charger circuit 620 to control the charging of the LiPo battery 408. The microcontroller also controls the operation of the motor voltage generator 622 in a similar manner. The microcontroller controls the heater driver 610 and the motor drivers 612 in response to commands received from a user. The microcontroller monitors a voltage responsive to the resistance of the thermistor 360 and selectively turns on and turns off the heater driver to maintain the temperature of the heat generation unit 130 within a selected temperature range.

The microcontroller 630 also controls the information displayed on the LCD panel 430 via a display controller 640. The microcontroller sends signals to the display controller representing the information to be displayed. The display controller receives the signals and generates the required command and data signals to the LCD to properly display the information. As discussed above, the displayed information includes the start and stop icons, the temperature icon with the three level icons, the vibration icon with the three vibration mode icons, and the timer icon with the 10 time bars. The control of an LCD is well-known in the art and is not described in detail herein. In the illustrated embodiment, the display controller is incorporated into the microcontroller. In other embodiments, the display controller may be a separate controller.

The microcontroller 630 receives signals from the touch panel 440 via a touch panel controller 650, which is located on the second PCB 420 in the illustrated embodiment. In the illustrated embodiment, the microcontroller communicates with the touch panel controller via a conventional I²C bus. The microcontroller is responsive to signals from the touch panel controller that represent touching of the touch panel in areas corresponding to the icons displayed on the underlying LCD panel 430. The microcontroller is not responsive to touching of areas of the touch panel that do not correspond to a displayed icon. In the illustrated embodiment, the touch panel controller comprises a YS812A touch sensing microcontroller, which is commercially available from Taiwan Hui Electronics Co., Ltd., in Taiwan.

As discussed above, the microcontroller 630 is also responsive to the first pushbutton switch 422 and the second pushbutton switch 424. When the microcontroller is off and the first pushbutton switch is activated, the microcontroller awakens from a low power mode and generates the signals required to display the icons on the LCD panel 430. The microcontroller waits for signals from the touch panel 440 via the touch panel controller 650. If a touch signal is received corresponding to the location of the start icon, the microcontroller becomes responsive to the touch signals from the heat selection icons and the vibration selection icons as described above. When the first pushbutton switch is activated while the microcontroller is active, the microcontroller turns off all functions and reenters the low-power state.

The microcontroller 630 is also responsive to the second pushbutton switch 424. Each time the second pushbutton switch is activated, the main controller toggles between a first display state and a second display state. In the first display state, the microcontroller sends a command to reduce the brightness of the LCD panel 430. In the first display state, the microcontroller is not responsive to any touch signals from the touch panel 440 via the touch panel controller 650. When the second pushbutton switch is activated when the microcontroller is in the first display state, the microcontroller responds by switching to the second display state wherein the microcontroller sends a command to increase the brightness of the icons of the LCD panel. While in the second display state, the microcontroller is responsive to touch signals from the touch panel via the touch panel controller. In the illustrated embodiment, the microcontroller automatically reenters the first display state after a selected period of inactivity (e.g., approximately 5 seconds) when the user does not touch an active portion of the touch panel. In the first display state, the reduction in brightness of the LCD saves energy; and the microcontroller is not responsive to any inadvertent touching of the touch panel.

The microcontroller 630 further sends commands to the LCD panel 430 to cause the LCD panel to display selected graphics as described above. In addition to sending commands to generate the static display icons shown in FIG. 17, the microcontroller also sends commands to selectively illuminate the ring icons that represent the current selected operational state (e.g., temperature setting low, medium or high; and vibration setting wave, pulse or constant). The microcontroller also updates the timer bar icons to display the remaining time before the microcontroller automatically turns off.

The microcontroller 630 receives commands from the touch panel 440 via the touch panel controller 650 when a user touches an active area of the touch panel. The microcontroller is responsive to the received commands to selectively control the operations of the four vibration pods 120, 122, 124, 126 and to control the operation of the heat generation unit 130.

The microcontroller 630 controls the first vibration pod 120 by selectively providing the motor voltage (e.g., approximately 12 volts DC) to the first vibration pod. In the illustrated embodiment, the microcontroller activates one or more of the motor drivers 612 to provide respective return paths to ground. The other three vibration pods 122, 124, 126 are controlled in a similar manner. The microcontroller controls the heat generation unit 130 by selectively providing the battery voltage (e.g., approximately 16.8 volts DC) to the heat generation unit. In the illustrated embodiment, the microcontroller activates the heater driver 610 to provide a return path to ground. The microcontroller is responsive to the resistance of the thermistor 360 to maintain the temperature within a range selected by the currently active temperature mode. As noted above, the thermal cutoff switch 350 embedded in the heat generation unit independently opens the current path to the heat generation unit if the temperature of the heat generation unit exceeds approximately 80 degrees Celsius.

As further shown in FIG. 18, the vibration and heat generation apparatus 100 may also be controlled by a Bluetooth interface 660 coupled to a smartphone (not shown) or other device having a Bluetooth compatible interface. For example, in one embodiment, the Bluetooth interface is connected to the microcontroller 630 to send commands to and to receive information from the microcontroller. The Bluetooth interface is controlled by an application (App) running on the smartphone (or other device) that presents a user with a display screen having icons corresponding to the icons shown in FIG. 17. When a user touches the icons on the smartphone display, the commands are sent to the microcontroller via the coupled Bluetooth interfaces to control the microcontroller in a manner corresponding to the control of the microcontroller by the touch panel controller 650. The microcontroller responds by selecting the requested mode and by sending a confirmation to the smartphone App that the command has been received and has been implemented on the vibration and heat generation apparatus. The Bluetooth interface is particularly useful when the vibration and heat generation unit is positioned on a user's body in a location where the LCD display 430 is not easily viewed by the user.

Figure 19:
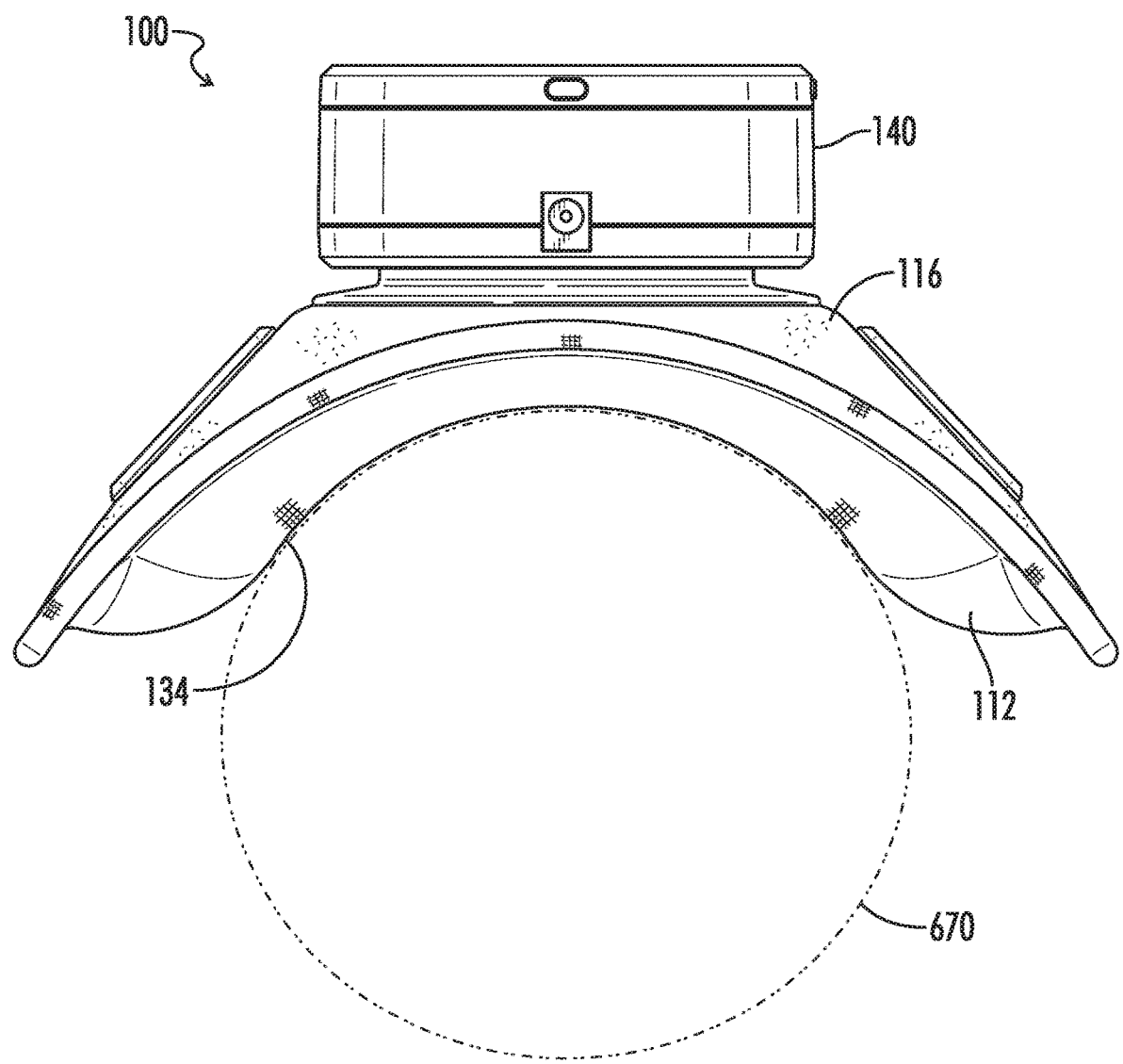
FIG. 19 illustrates an elevational view of the vibration and heat generation apparatus of FIG. 1 showing the flexing of the upper support structure and the bag-like lower housing to conform the apparatus to a cylindrical object such as a human limb.

As shown in FIG. 19, the vibration and heat generation apparatus 100 is sufficiently flexible to bend around a generally cylindrical object 670 such as, for example, a human limb or joint (represented in dashed lines). The flexible lower bag-like structure 112 readily conforms to the contours of the limb or joint. The upper support structure 116 forms the outer boundary of the bent apparatus and positions the vibration pods and heat generating unit (within the enclosure 110) against the joint or limb receiving therapy. In addition to having an overall size and shape resembling a conventional flattened ice bag, the vibration and heat generation apparatus conforms to a human body part in a manner similar to an ice bag.

The vibration and heat generation apparatus 100 disclosed herein is configured for use with compression wraps that are used to apply compression to an ice bag positioned against a portion of a mammalian (e.g., human) body to provide therapeutic cooling. Such compression wraps are disclosed in U.S. Pat. No. 9,289,323, for "Ice Bag with Air Release Valve for Therapeutic Treatment, which issued on Mar. 22, 2016, and which is incorporated herein by reference in its entirely. FIGS. 12-15 of the referenced patent illustrate compression wraps used to apply compression to an ice bag applied to a person's hip (FIG. 12), to a person's knee (FIG. 13), to a person's left shoulder (FIG. 14) and to a person's right shoulder (FIG. 15). FIG. 16 of the referenced patent illustrates a compression wrap used to apply compression to a first ice bag applied to the front of a person's left shoulder and to apply compression to a second ice bag applied to the back of a person's left shoulder. FIGS. 17A and 17B of the referenced patent illustrate the application of two ice bags to a person's left shoulder using the compression wrap of FIG. 16.

Figure 12:
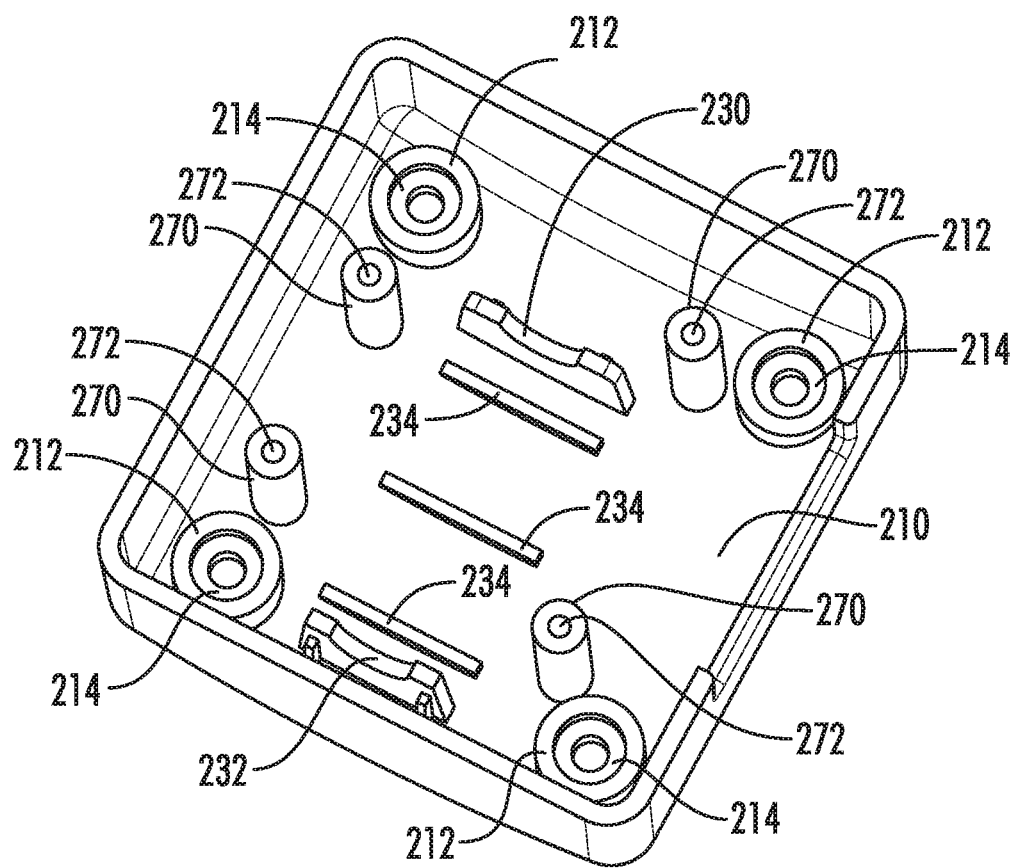
FIG. 12 illustrates an upper perspective view of the lower cover of the vibrational pod of FIG. 9 rotated by a small angle to show addition features of the cavity of the lower cover.
Figure 13:
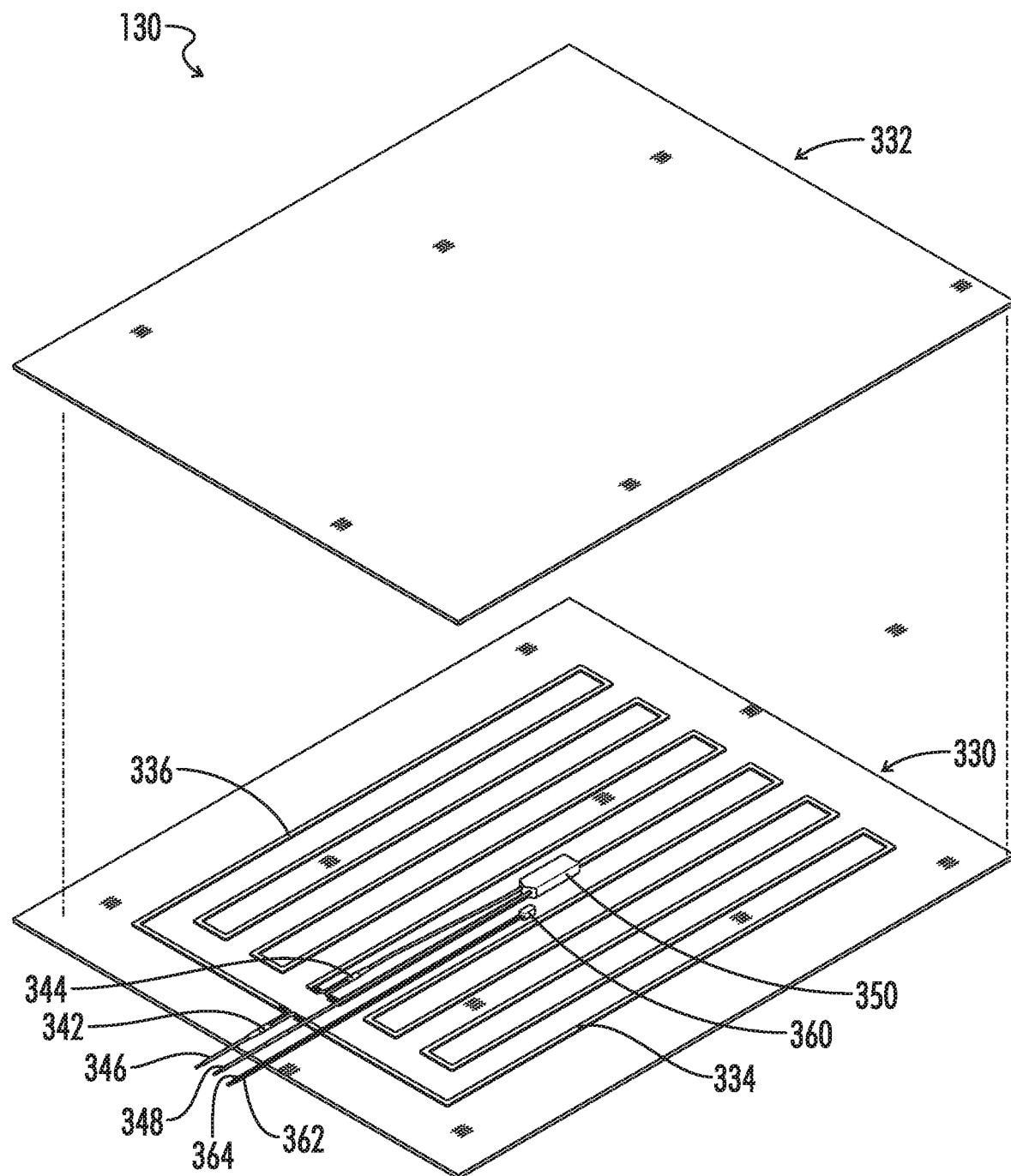
FIG. 13 illustrates an exploded upper perspective view of the heating pad of the vibration and heat generation apparatus showing the heating elements, the temperature sensor and the thermal cutoff switch on the lower sheet of the heating pad.
Figure 20:
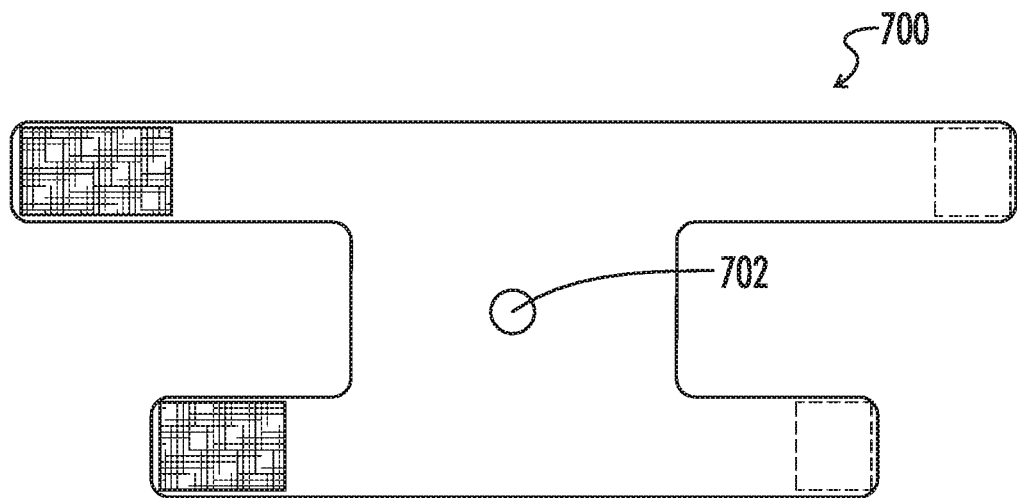
FIG. 20 illustrates an elevational view of a compression wrap configured to be attached to a person proximate to the person's hip, the compression wrap including a circular bore to receive the control unit of the vibration and heat generation unit of FIG. 1.
Figure 21:
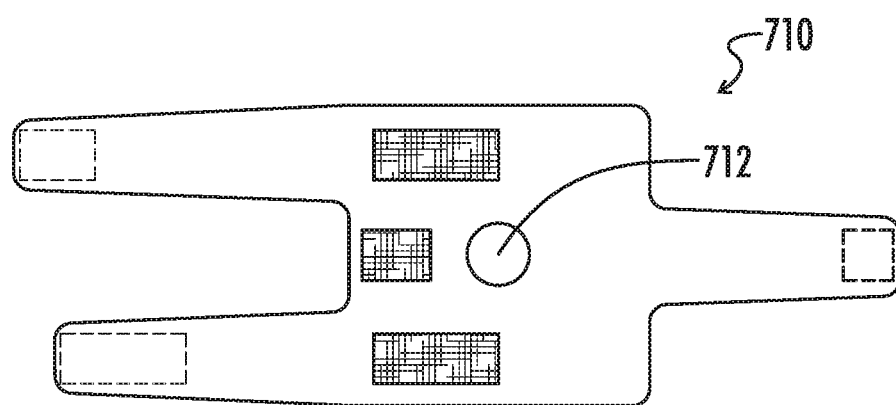
FIG. 21 illustrates an elevational view of a compression wrap configured to be attached to a person proximate to the person's knee, the compression wrap including a circular bore to receive the control unit of the vibration and heat generation unit of FIG. 1.
Figure 22:
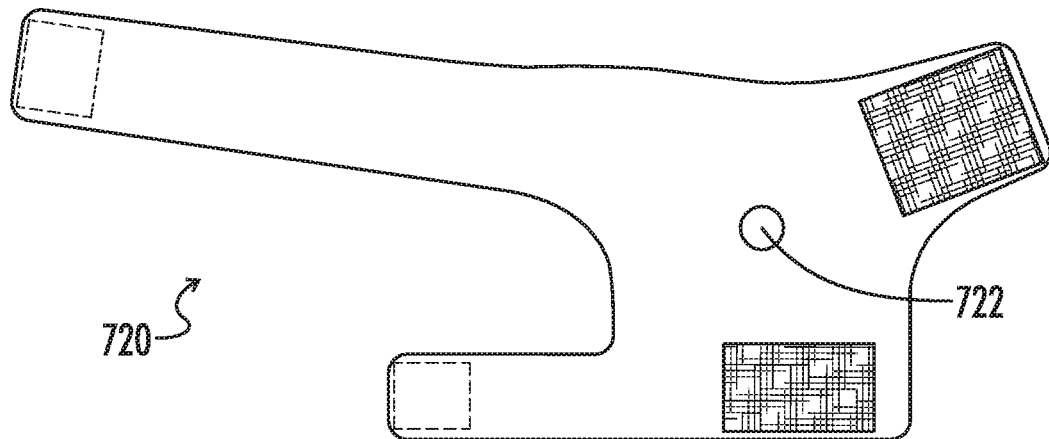
FIG. 22 illustrates an elevational view of a compression wrap configured to be attached to a person proximate to the person's left shoulder, the compression wrap including a circular bore to receive the control unit of the vibration and heat generation unit of FIG. 1.
Figure 23:
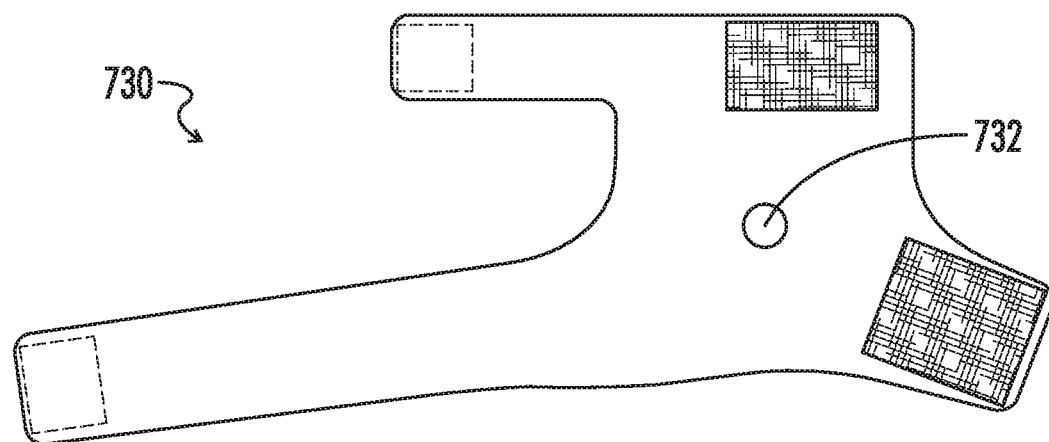
FIG. 23 illustrates an elevational view of a compression wrap configured to be attached to a person proximate to the person's right shoulder, the compression wrap including a circular bore to receive the control unit of the vibration and heat generation unit of FIG. 1.
Figure 24:
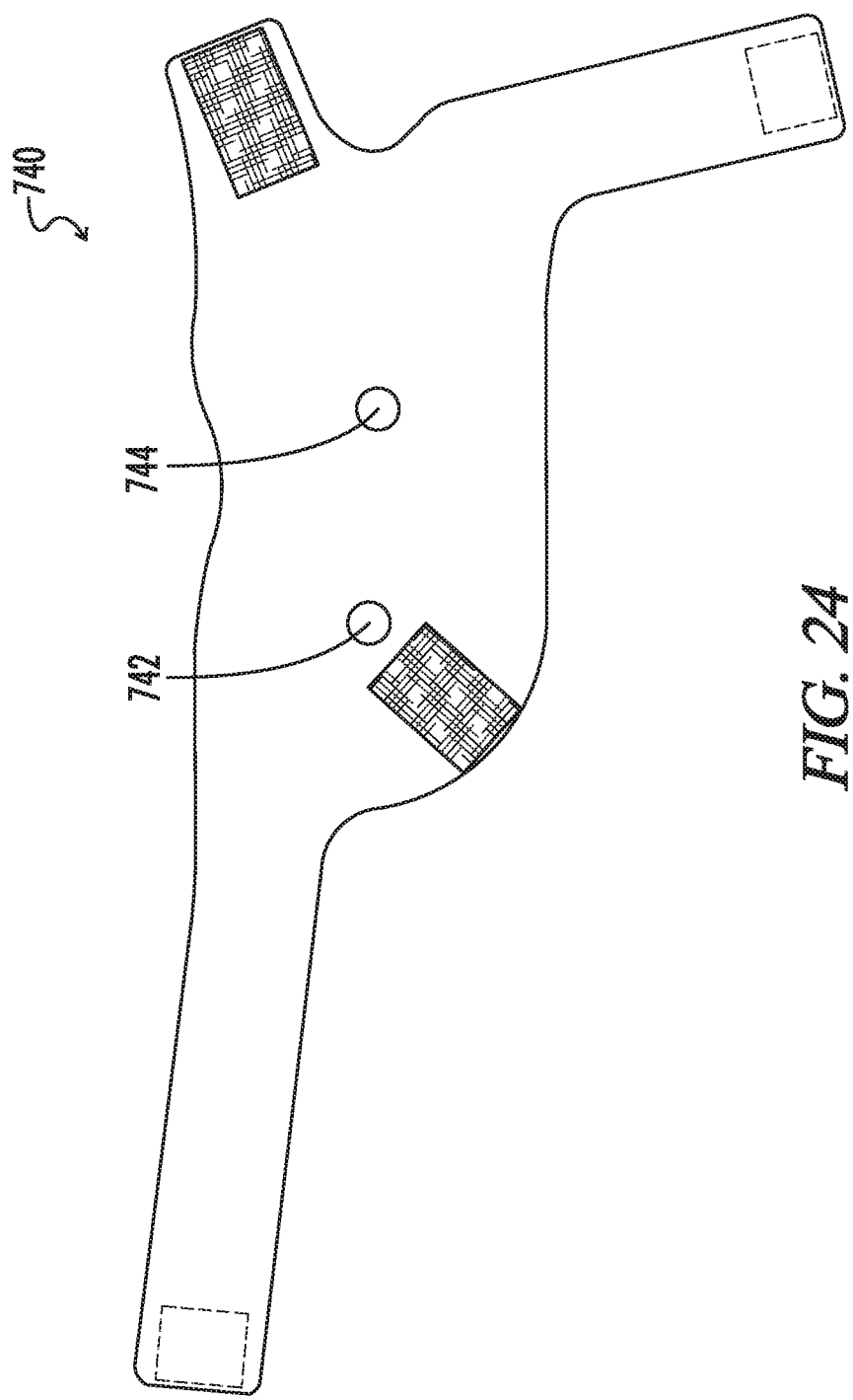
FIG. 24 illustrates an elevational view of a compression wrap configured to be attached to a person proximate to the person's left shoulder, the compression wrap including a first circular bore and a second circular bore, each circular bore configured to receive the control unit of a respective vibration and heat generation unit of FIG. 1.

The hip compression wrap of FIG. 12 of the referenced patent is reproduced herein as a hip compression wrap 700 of FIG. 20. The hip compression wrap includes a circular bore 702 sized to receive the neck of the ice bag described in the referenced patent. The knee compression wrap of FIG. 13 of the referenced patent is reproduced herein as a knee compression wrap 710 of FIG. 21 having a circular bore 712 sized to receive the neck of the ice bag described in the referenced patent. The left shoulder compression wrap of FIG. 14 of the referenced patent is reproduced herein as a left shoulder compression wrap 720 of FIG. 22 having a circular bore 722 sized to receive the neck of the ice bag described in the referenced patent. The right shoulder compression wrap of FIG. 15 of the referenced patent is reproduced herein as a right shoulder compression wrap 730 of FIG. 23 having a circular bore 732 sized to receive the neck of the ice bag described in the referenced patent. The two ice bag version of the left shoulder compression wrap of FIG. 16 of the referenced patent is reproduced herein as a compression wrap 740 of FIG. 24 having a first circular bore 742 sized to receive the neck of a first ice bag described in the referenced patent and having a second circular bore 744 sized to receive the neck of a second ice bag described in the referenced patent.

The cylindrical control unit 140 of the vibration and heat generation apparatus 100 has a shape and size selected to resemble an ice bag, such as, for example, the ice bag illustrated in the above-referenced U.S. Pat. No. 9,289,323. The selected shape and size enables the vibration and heat generation unit to be operable in combination with each of the compression wraps. The cylindrical control unit has a diameter of between about 50 millimeters and approximately 100 millimeters. For example in the illustrated embodiment, the control unit has a diameter of approximately 94 millimeters. The cylindrical bores in the existing compression wraps have diameters of approximately 45 millimeters. The material around the cylindrical bores easily stretches to accommodate the control unit and to hold the control unit snugly thereafter. The sizes of the cylindrical control unit and the sizes of the cylindrical bores can be varied; however, the illustrated dimensions provide a combination of sizes wherein the upper surface of the control unit has a sufficiently large size to accommodate the display and touch panel with icons of sufficient size to be easily manipulated while being sufficiently small to be inserted into a cylindrical bore that is able to receive and restrain the neck of a conventional ice bag or the ice bag shown in the referenced U.S. Pat. No. 9,289,323. By selecting the diameter of the control unit to be in a range of approximately 1.5 times to 3 times the diameter of the circular bore in a compression wrap, the compression wrap is able to stretch by a sufficient amount to accommodate the control unit without damaging the compression wrap and to exert a sufficient force on the control unit to secure the vibration and heat generation unit to the compression wrap while the compression wrap is being secured to the selected limb or joint of a person as described below.

Figure 25:
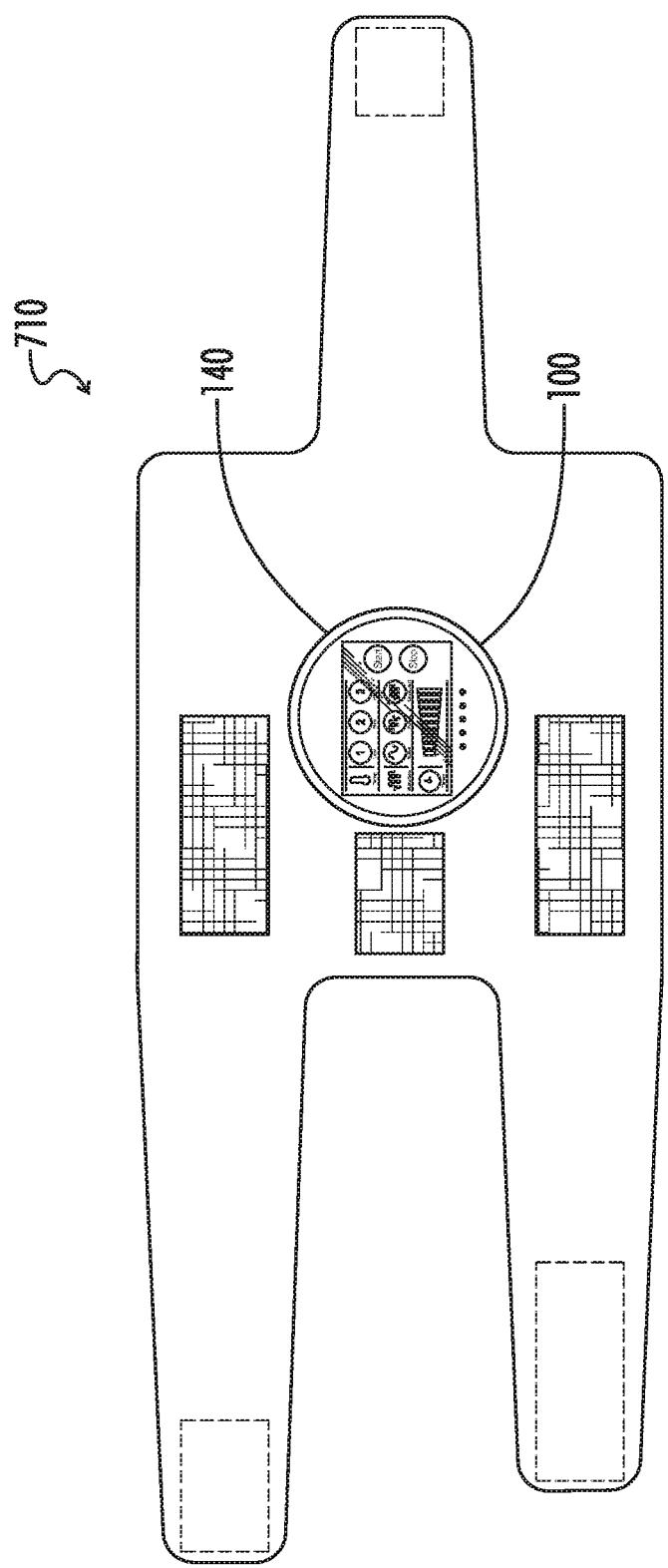
FIG. 25 illustrates an elevational view of the compression wrap of FIG. 21 with the control unit of the vibration and heat generation unit of FIG. 1 extending through the circular bore.
Figure 26:
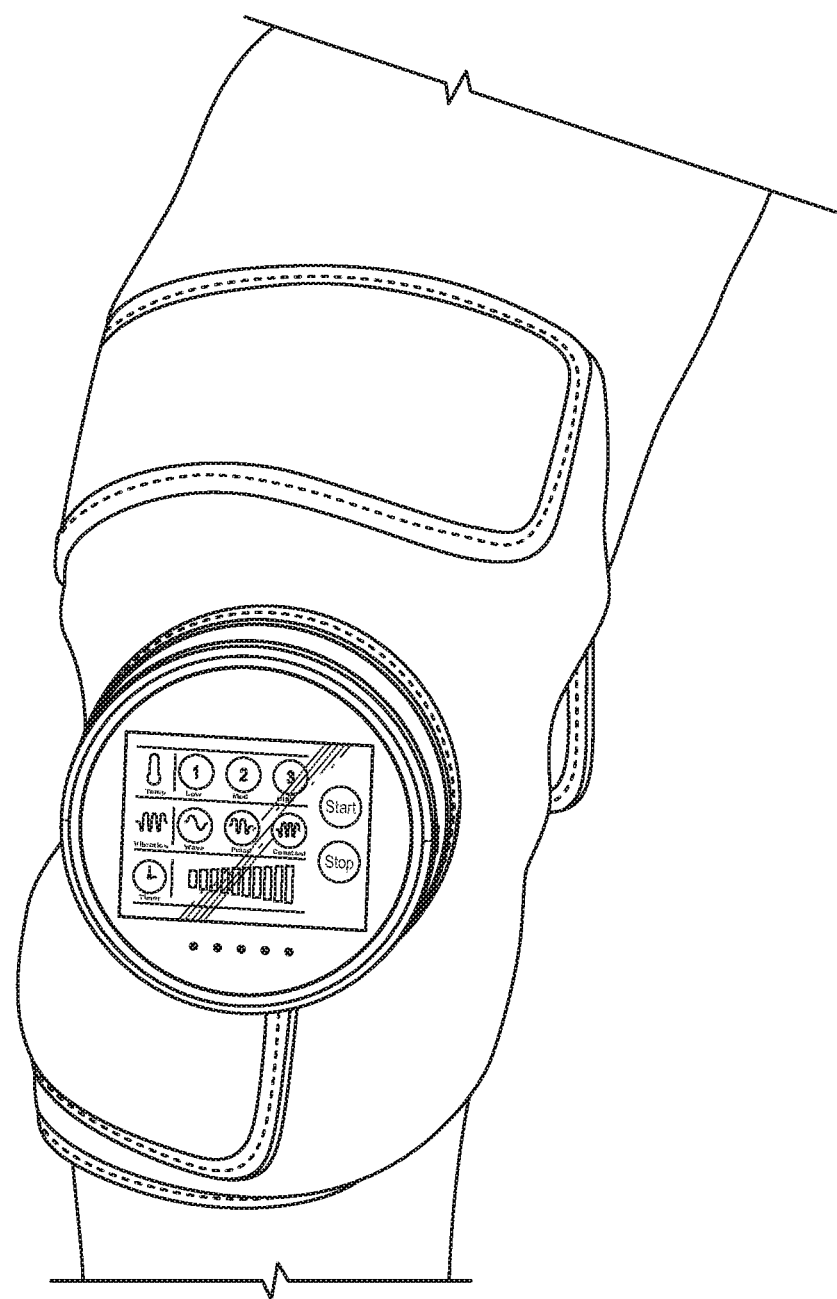
FIG. 26 illustrates a perspective view of the compression wrap and vibration and heat generation unit of FIG. 25 secured to a person's knee.

The control unit 140 of the vibration and heat generation apparatus 100 is inserted through the respective circular bore of one of the compression wraps of FIGS. 19-23. For example, FIG. 25 illustrates the vibration and heating apparatus in combination with the knee compression wrap 710 of FIG. 21 to apply vibration and heat to a person's knee. FIG. 26 illustrates the compression wrap and the vibration and heat generation apparatus applied to a knee. FIG. 27 illustrates a first vibration and heat generation apparatus 100A and a second vibration and heat generation apparatus 100B in combination with the compression wrap 740 of FIG. 23 to apply vibration and heat to the front and rear portions of a person's left shoulder. FIG. 28 illustrates a front view showing the compression wrap and the first vibration and heat generation apparatus on the person's left shoulder. FIG. 29 illustrates a rear view of the compression wrap and the second vibration and heat generation apparatus on the person's left shoulder.

The vibration and heat generation apparatus 100 described herein advantageously allows a person having a compression wrap useable with an ice bag for therapeutic cooling to remove the ice bag and install control unit 140 of the vibration and heat generation apparatus into the opening that receives the neck of the ice bag to provide therapeutic vibration and heat using the same compression wrap. Accordingly, a person does not have to have a separate compression wrap for each type of therapeutic treatment.

As various changes could be made in the above constructions without departing from the scope of the invention, it is intended that all the matter contained in the above description or shown in the accompanying drawings shall be interpreted as illustrative and not in a limiting sense.

What is claimed is:

1. A portable vibration and heat generation apparatus comprising:
   a flexible support platform;
   a cylindrical control unit mounted to a central portion of the support platform and extending perpendicularly from the support platform in a first direction, the control unit housing electronic circuitry and at least one battery;
   a plurality of vibration pods attached to the flexible support platform, each vibration pod extending from the support platform in a second direction, the second direction opposite the first direction, the vibration pods electrically connected to the control unit;
   a heat generation unit positioned below the vibration pods, the heat generation unit electrically connected to the control unit; and
   a bag-shaped enclosure, the bag-shaped enclosure attached to the support platform and enclosing the plurality of vibration pods and the heat generation unit, the bag-shaped enclosure having a distal wall, the heat generation unit positioned adjacent to the distal wall.

2. The portable vibration and heat generation apparatus as defined in claim 1, wherein each vibration pod includes an electrical motor having a shaft coupled to an eccentric mass.

3. The portable vibration and heat generation apparatus as defined in claim 1, wherein the plurality of vibration pods comprises four vibration pods, the four vibration pods arranged generally symmetrically about the cylindrical control unit.

4. The portable vibration and heat generation apparatus as defined in claim 1, wherein the heat generation unit comprises at least one resistance heating wire secured to a flexible sheet, the resistance heating wire generating heat when a current flows through the heating wire.

5. The portable vibration and heat generation apparatus as defined in claim 4, wherein the heat generation unit is operable at at least a first temperature setting, a second temperature setting and a third temperature setting.

6. The portable vibration and heat generation apparatus as defined in claim 1, wherein the control unit is responsive to a signal received via a wireless communication interface.

7. The portable vibration and heat generation apparatus as defined in claim 6, wherein the wireless communication interface is a Bluetooth® interface.

8. A system for applying compression, vibration and heat to a body part of a person, comprising:
  a portable vibration and heat generation apparatus comprising
    a flexible support platform,
    a cylindrical control unit mounted to a central portion of the support platform and extending perpendicularly from the support platform in a first direction, the control unit housing electronic circuitry and at least one battery,
    a plurality of vibration pods attached to the flexible support platform, each vibration pod extending from the support platform in a second direction, the second direction opposite the first direction, the vibration pods electrically connected to the control unit,
    a heat generation unit positioned distal to the vibration pods, the heat generation unit electrically connected to the control unit, and
    a bag-shaped enclosure, the bag-shaped enclosure attached to and extending distally from the support platform, the bag-shaped enclosure enclosing the plurality of vibration pods and the heat generation unit, the bag-shaped enclosure having a distal wall, the heat generation unit positioned adjacent to the lower wall; and
  a compression wrap comprising a unitary sheet of elastic material having a central body with straps extending therefrom, the central body including at least one bore that receives the cylindrical control unit of the portable vibration and generation apparatus therethrough, the straps positionable with respect to the body part of the person to secure the distal wall of the bag-shaped enclosure of the portable vibration and generation apparatus against the body part to apply heat from the heat generation unit to the body part and to apply vibration from the vibration pods to the body part.

9. A system for applying a combination of compression, vibration and heat to a body part of a person, the system comprising:
  a portable vibration and heat generation apparatus including
    a flexible support platform having an outer perimeter,
    a bag-shaped enclosure having a perimeter attached to the outer perimeter of the support platform, the bag-shaped enclosure extending distally from the support platform in a first direction to a distal wall,
    a cylindrical control unit mounted to the support platform and extending perpendicularly and proximally from the support platform in a second direction opposite the first direction, the control unit housing electronic circuitry and at least one battery, the control unit including a panel having a plurality of touch responsive areas thereon to receive commands to control the electronic circuitry,
    a plurality of vibration pods, each vibration pod having at least a portion extending from the support platform in the first direction and enclosed within the bag-shaped enclosure, and
    a heat generation unit enclosed within the bag-shaped enclosure and positioned proximate to the distal wall of the bag-shaped enclosure; and
  a compression wrap having a bore formed therethrough, the cylindrical control unit of the portable vibration and heat generation apparatus extending through the bore, the compression wrap securable to a body part with the distal wall of the bag-shaped enclosure against the body part.

* * * * *